(12) United States Patent
Czaja

(10) Patent No.: US 11,612,787 B2
(45) Date of Patent: Mar. 28, 2023

(54) METHOD AND APPARATUS FOR ANALYSIS OF GAIT AND TO PROVIDE HAPTIC AND VISUAL CORRECTIVE FEEDBACK

(71) Applicant: IPComm LLC, Cardiff, CA (US)

(72) Inventor: Stanislaw Czaja, Cardiff, CA (US)

(73) Assignee: IPCOMM, Cardiff, CA (US)

( * ) Notice: Subject to any disclaimer, the term of this patent is extended or adjusted under 35 U.S.C. 154(b) by 269 days.

(21) Appl. No.: 16/897,163

(22) Filed: Jun. 9, 2020

(65) Prior Publication Data

US 2020/0298058 A1 Sep. 24, 2020

Related U.S. Application Data

(63) Continuation of application No. 15/464,083, filed on Mar. 20, 2017, now abandoned, which is a
(Continued)

(51) Int. Cl.
*G09B 19/00* (2006.01)
*A43B 5/04* (2006.01)
(Continued)

(52) U.S. Cl.
CPC ............ *A63B 24/0006* (2013.01); *A43B 3/34* (2022.01); *A43B 5/00* (2013.01); *A43B 5/04* (2013.01); *A43B 5/0405* (2013.01); *A43B 5/16* (2013.01); *A43B 5/1616* (2013.01); *A43B 17/00* (2013.01); *A61B 5/112* (2013.01); *A61B 5/1124* (2013.01); *A61B 5/6807* (2013.01); *A63B 71/0622* (2013.01); *A63C 3/00* (2013.01); *A63C 11/003* (2013.01); *G06F 3/011* (2013.01); *G06F 3/016* (2013.01); *G06V 40/25* (2022.01); *G09B 5/02* (2013.01); *G09B 19/0038* (2013.01); *G16H 20/30* (2018.01); *G16H 40/63* (2018.01); *G16H 40/67* (2018.01); *A61B 5/0024* (2013.01); *A61B 5/7225* (2013.01); *A61B 2503/10* (2013.01);
(Continued)

(58) Field of Classification Search
CPC ..... A61B 5/1038; A61B 5/112; A61B 5/1121; A61B 5/6807; A61B 5/7455; A61B 2562/0219; A61B 2562/0223; A61B 2562/0247; A61B 2090/064; A43B 3/34; A43B 3/38; A63B 2220/12; A63B 2220/40; A63B 2220/53; A63B 2220/836; A63B 2225/50; A63B 26/003
See application file for complete search history.

(56) References Cited

U.S. PATENT DOCUMENTS 9,526,946 B1 * 12/2016 Zets .................. A61B 5/4023
2010/0063778 A1 * 3/2010 Schrock ............. A63B 24/0062
73/172
(Continued)

*Primary Examiner* — Lawrence S Galka

(57) ABSTRACT

A system for analysis of user gait and to provide correction in form of haptic and visual feedback. This system comprises a motion and force sensors and a haptic actuator embedded in the user shoe insoles in communication with a smart-phone based analysis application, configured to calculate motion and orientation of the user feet in relation to the value, location and distribution of ground reaction forces measured by sensors located in the shoe insoles and after analysis of said forces and motion, to provide haptic feedback to the user foot instructing about the location (and timing) of pressure the user must apply to achieve an optimal gait.

9 Claims, 20 Drawing Sheets

Related U.S. Application Data continuation-in-part of application No. 14/747,179, filed on Jun. 23, 2015, now Pat. No. 9,968,840.

(51) Int. Cl.

| | | |
|---|---|---|
| A63B 24/00 | (2006.01) | |
| A43B 5/14 | (2006.01) | |
| A43B 5/16 | (2006.01) | |
| A43B 3/00 | (2022.01) | |
| G01L 1/14 | (2006.01) | |
| A43B 5/00 | (2022.01) | |
| A43B 17/00 | (2006.01) | |
| A63B 71/06 | (2006.01) | |
| G09B 5/02 | (2006.01) | |
| A63C 11/00 | (2006.01) | |
| G06F 3/01 | (2006.01) | |
| A61B 5/11 | (2006.01) | |
| A61B 5/00 | (2006.01) | |
| A63C 3/00 | (2006.01) | |
| G16H 20/30 | (2018.01) | |
| G16H 40/63 | (2018.01) | |
| G16H 40/67 | (2018.01) | |
| A43B 3/34 | (2022.01) | |
| G06V 40/20 | (2022.01) | |
| A63B 69/18 | (2006.01) | |
| G01S 19/19 | (2010.01) | |
| H04M 1/72412 | (2021.01) | |

(52) U.S. Cl.
CPC ... *A61B 2505/09* (2013.01); *A61B 2562/0219* (2013.01); *A61B 2562/0247* (2013.01); *A63B 69/18* (2013.01); *A63B 2071/0636* (2013.01); *A63B 2071/0655* (2013.01); *A63B 2220/12* (2013.01); *A63B 2220/16* (2013.01); *A63B 2220/36* (2013.01); *A63B 2220/40* (2013.01); *A63B 2220/44* (2013.01); *A63B 2220/56* (2013.01); *A63B 2220/62* (2013.01); *A63B 2220/74* (2013.01); *A63B 2220/803* (2013.01); *A63B 2220/836* (2013.01); *A63B 2220/89* (2013.01); *A63B 2225/02* (2013.01); *A63B 2225/20* (2013.01); *A63B 2225/50* (2013.01); *A63B 2225/54* (2013.01); *A63B 2244/19* (2013.01); *A63C 2203/12* (2013.01); *A63C 2203/18* (2013.01); *A63C 2203/22* (2013.01); *A63C 2203/24* (2013.01); *G01S 19/19* (2013.01); *H04M 1/72412* (2021.01)

(56) References Cited

U.S. PATENT DOCUMENTS

| | | | |
|---|---|---|---|
| 2013/0217998 A1* | 8/2013 | Mahfouz | A61B 5/0004 600/595 |
| 2016/0287937 A1* | 10/2016 | Fitzgerald | A61B 5/1122 |
| 2016/0335913 A1* | 11/2016 | Grant | A43B 5/0401 |
| 2016/0338621 A1* | 11/2016 | Kanchan | A61B 5/486 |
| 2017/0119551 A1* | 5/2017 | Huang | A61F 2/72 |
| 2017/0143261 A1* | 5/2017 | Wiedenhoefer | A61B 5/0086 |
| 2018/0368737 A1* | 12/2018 | Bonomi | A61B 5/02438 |

\* cited by examiner

METHOD AND APPARATUS FOR ANALYSIS OF GAIT AND TO PROVIDE HAPTIC AND VISUAL CORRECTIVE FEEDBACK

CROSS-REFERENCE OF RELATED APPLICATIONS—CLAIM OF PRIORITY

This application is a continuation of, and claims the benefit of priority under 35 USC § 120 of, prior U.S. application Ser. No. 15/464,083, filed Mar. 20, 2017, entitled "Method and Apparatus for Analysis of Gait and to Provide Haptic and Visual Corrective Feedback", the disclosure of which is incorporated herein by reference in its entirety; application Ser. No. 15/464,083 is a Continuation in Part application of non-provisional application Ser. No. 14/747,179 titled "Method and Apparatus to Provide Haptic and Visual Feedback of Skier Foot Motion and Forces Transmitted to the Ski Boot" filed Jun. 23, 2015, which application issued May 15, 2018 as U.S. Pat. No. 9,968,840; this continuation application claims priority to all of the above-cited patent applications and issued patent, and the cited applications and issued patent are all incorporated by reference in their entirety as though fully and completely set forth herein.

FIELD OF THE INVENTION

The present invention relates to the field of visualization of motion, weight distribution and forces transferred by the feet to the insole of the user shoe. Such invention may be used for the purpose of monitoring forces projected through the foot to the ski or snowboard to the snow or an athlete shoe to aid in training and performance evaluation, or to the sole of a shoe to allow analysis or user gait in order to correct the user walking pattern or aid in the recovery after physical injuries. Said analysis is achievable by embedding a gyroscope, accelerometer, magnetometer, pressure and force sensors into the insole (or sole) of the shoe to provide measurement of foot rotational and lateral motions in relation to forces transmitted from the foot. Furthermore, one or more actuators are embedded in the shoe insole to provide haptic feedback to the user foot. The motion and weight distribution vectors are processed by the micro-controller embedded in the insole, and the resulting motion matrices are transmitted to the user smart-phone using Bluetooth, or other suitable short range radio interface. Alternatively, the data from motion sensors may be transmitted to the user smart-phone for processing of motion fusion matrices. The results are synchronized to GPS time and coordinates, then after applying appropriate filtering, transmitted to one or more actuators embedded in the shoe insole, providing haptic feedback to the user, indicating timing and direction of force distribution required to execute turn or to correct running or walking pattern. The results may also be transmitted to the remote location ("cloud service") for further processing using user's smart-phone cellular radio interface. Said processing includes presenting of the foot motion and force distribution in a form of animation and superimposition of motion and force data on the 3D maps obtained from GPS coordinates. The post-processed visual and numeric data may then be received from the cloud server by the user smart-phone or by a remote computer terminal. Furthermore, if a devotion, such as: accident; fall without recovery over certain period of time is detected, an SMS message informing of such situation is sent with the corresponding data to the predefined recipients.

BACKGROUND

In skiing as well as gait analysis, monitoring of performance relies on few techniques, such as: user feelings, instructor/coach observations, etc, and some empirical factors, such as: time measurements and video analysis, however, most of those techniques are not practical for the every day training or improve in diagnostics and recovery of physical injuries, as they require bulky equipment, large team of highly skilled technicians while lacking sufficient amount of data and have no ability to provide corrective, real-time feedback.

The comfort, safety and pleasure of skiing or running or the recovery period of motion skills are highly dependent on amount of data; the quality of said data analysis; and the efficiency of the corrective feedback. While most athletes relay on advise from a coach, most recreational athletes relay solely of self-observation. To analyze gait of individuals recovering from serious injuries or of an athlete, a trained therapists obtain data in a controlled laboratory environment employing several video or infrared cameras placed around a walkway. The subject of analysis (patient or an athlete) has markers located at various points of reference of the body and data is collected, analyzed by professional who provides feedback to the subject and/or therapist. To measure kinetics—ground reaction forces, lab may have floor-mounted load transducers. Due to complexity of the said measurement system, collected data rarely correlates with normal activity of the subject while the feedback is delayed. In the past, some innovation in recording the pressure points projected by the foot on the shoe insole were introduced in an attempt to analyze bio-mechanics of training and gait. However, those devices record only distribution of pressure while requiring synchronization with real-time video to provide meaningful information. And as real-time video synchronization is rarely available outside of the lab, the benefit of such devices is very limited.

In recent years, the use of mobile devices and, in particular, smart-phones proliferated, all provided by the progress in electronics circuit integration. Today's smart-phone besides providing communication over cellular network is equipped with various input/output capabilities, such as wireless PAN (Personal Area Network), and provides significant computing resources. Such computing and communication resources may be integrated with a motion analyzer embedded into replaceable sole of a ski boot, or a walking/running shoe, or a skate boot, etc, to provide level and quality of feedback suitable for all—from an athlete trying to improve his performance to a patient trying to recover form an injury. In such system, a motion and force analyzer embedded in the insole communicating with the user smart-phone or a dedicated cellular interface modem, provides capability to record, analyze and visualize all characteristic movement, ground reaction forces transferred to the user foot and to provide corrective feedback to the user. The characteristic may be transmitted to the remote location using smart-phone cellular radio interface and stored in the "Internet cloud" for post-analysis or displayed in real-time in a remote location. Such system can be used as an aid in instruction or in recover, or as a tool in objective determination of athlete performance—i. e. to determine quality of performance by the free-style skier. Such system may operate using any of wireless technology such as: cdma2000, UMTS, WiMax, LTE. LTE-A, etc.

SUMMARY OF THE INVENTION

This invention describes system which allows visualization of user's foot motion in relation to the distribution pressure points inside the shoe and to provide real-time corrective haptic feedback by embedding miniature micromechanical systems (MEMS) and electronics components into the inner sole of the shoe. The system comprises of: 3-axis accelerometer, 3-axis gyroscope and a 3-axis magnetometer, to provide motion vectors in 9-degree of freedom, to obtain 3-D motion, and a multiplicity of force-pressure sensors—to record forces transmitted from the foot to the insole or ground reaction forces transmitted to the foot. In addition, an atmospheric pressure sensor providing measurement of changes of atmospheric pressure (to record vertical motion), may be added. Such system provides measurement of linear acceleration, rotational vectors and orientation (attitude) in three-dimensional space does provides representation of motion in relation to ground reaction forces. This motion and force vectors, synchronized with GPS time and coordinates are sent to a remote location for processing and presentation in visual and numerical form. Such presentation may be used to understand the precise cause—in relation to time/position to aid in training or to provide corrective feedback or provide explanation of the nature of error and to suggest remedy. Such corrective feedback may be in form of a feedback by a haptic actuator located under the user's toe(s) to provide haptic instructions how/when to change distribution of the forces in the shoe. This feedback is based on the analysis of the: current phase of the motion; information about the user and equipment and his physical parameters: current distribution of force inside shoe; and the knowledge of proper timing and the distribution of force required to achieve smooth transition of the desired motion. In addition, visual presentation of motion in 3D space and/or the topological information is added, providing objective assessment of the performance or rehabilitation.

The motion and force processing system of the present invention comprises motion capture sub-system consisting of: a multi-axis accelerometer; a gyroscope; a magnetometer (compass); a barometric pressure; a multiplicity of force sensors; a microprocessor; and a personal area network (PAN) radio interface to communicate motion vectors to the smart-phone based application.

According to first embodiment of this invention, the motion and force processing system is embedded in a replaceable insole of the ski boot inner-lining or directly embedded in the ski boot to analyze the motion of skis in relation to the location and value of force transferred by the skier feet to the insoles of the ski boot and the timing such force is applied.

It is well understood how ski or snowboard turns when moments are applied to the ski edge by skier's body through the forces applied to the skier's foot, and how the turning performance is determined by said forces and the reactions introduced by ski-snow contact. Understanding of skiing bio-mechanics allows determination of proper pressure distribution on the skier's foot in order to make the foot pronate to control the external forces that disturb equilibrium of balance. To establish balance platform, skier must place the center of pressure on the outside (of the turn) foot, and only in specific conditions during the turn. In the foot/skiboot system, the center of pressure (COP), lays at the point where the resulting force ($F_R$) of interaction between the ski and snow acting on a skier at ski between the turns (flat phase of turn), pulls his center of mass (COM) downward towards the snow and is opposed by muscles preventing a fall. Said knowledge may be augmented with real-time tracking of ski boot motion and the distribution of pressure points inside the ski boot during difference phases of turn.

Analyzing motion, one may determine the current phase of the turn and knowing the skier and equipment physical parameters may predict (extrapolate) the desired rate of ski rotation, then provide haptic stimulus indicating time the COP must be transferred form one part of the foot to another part. Such system, comprising motion and pressure sensors embedded in the ski boots and a smart-phone based application may provide real-time feedback to the skier and visual post-run analysis does provide tool in training.

According to second embodiment of this invention, the motion and force processing system is embedded in a replaceable insole of the walking or running shoe to analyze gait and balance of user by estimating vertical ground reaction force vector applied trough the shoe insoles to user's feet and limbs in relation to feet motion, then after said analysis provide haptic corrective feedback.

As the gait analysis is a function of modification of many movement factors, the gait patterns can be transient or permanent. As such the gait analysis system of this embodiment can aid both to provide information of natural abnormalities and help selection of suitable prosthetics, as well as in rehabilitation of a temporary gait abnormalities during the recover from physical injuries, such as cerebral palsy or recover of stroke patient, or add in training in order to optimize athlete performance.

This embodiment of the invention, allow for the assessment of gait disorders and effects of corrective orthopedic surgery, as well as to help in selection of options for treatment and correction of distorted bony anatomy such as a misaligned pelvis or sacrum.

BRIEF DESCRIPTION OF THE DRAWINGS

A better understanding of the present invention can be obtained when the following detailed description of the preferred embodiment is considered in conjunction with the following drawings, in which.

Figure 1A:
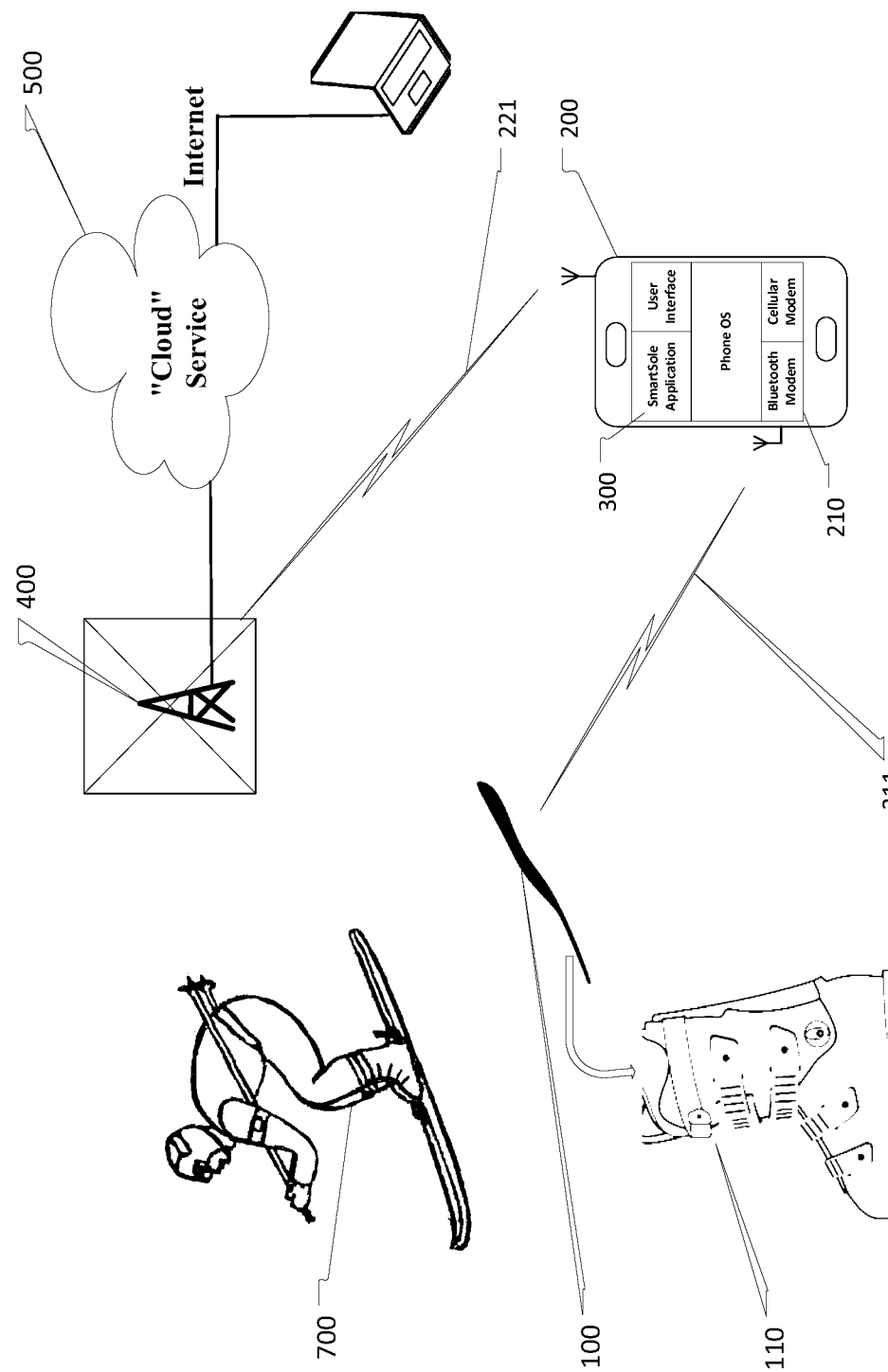
FIG. 1A, is an exemplary skiboot haptic feedback system.

While the invention is susceptible to various modifications and alternative forms, specific embodiments thereof are shown by way of example in the drawings and are herein described in detail. It should be understood, however, that the drawings and detailed descriptions are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE INVENTION

The following is a glossary of terms used in the present application:

Haptic Feedback System—in the context of this invention is a system able to collect and analyze motion and forces applied by the user foot to the insole of the shoe, then after determination of the phase of motion, apply a haptic feedback to the user's foot indicating optimal distribution of the pressure points.

Application—the term "application" is intended to have the full breadth of its ordinary meaning. The term "application" includes 1) a software program, which may be stored in a memory and is executable by a processor or 2) a hardware configuration program useable for configuring a programmable hardware element.

Computer System—any of various types of computing or processing systems, including mobile terminal, personal computer system (PC), mainframe computer system, workstation, network appliance, Internet appliance, personal digital assistant (PDA), television system, grid computing system, or other device or combinations of devices. In general, the term "computer system" can be broadly defined to encompass any device (or combination of devices) having at least one processor that executes instructions from a memory medium.

Mobile Terminal—in the scope of this invention any wireless terminal such as cell-phone, smart-phone, etc. provisioned to operate in the cellular network.

Memory Medium—Any of various types of memory devices or storage devices. The term "memory medium" is intended to include an installation medium, e.g., a CD-ROM, floppy disks 104, or tape device; a computer system memory or random access memory such as DRAM, DDR RAM, SRAM, EDO RAM, etc.; or a non-volatile memory such as a magnetic media, e.g., a hard drive, or optical storage. The memory medium may comprise other types of memory as well, or combinations thereof. In addition, the memory medium may be located in a first processor in which the programs are executed, or may be located in a second different processor which connects to the first processor over a network, such as wireless PAN or WMAN network or the Internet. In the latter instance, the second processor may provide program instructions to the first processor for execution. The term "memory medium" may include two or more memory mediums which may reside in different locations, e.g., in different processors that are connected over a network.

Near Field Communication (NFC)—in the scope of this invention is a type of radio interface for near communication.

Personal Area Network (PAN)—in the scope of this invention, is a personal are network radio interface such as: Bluetooth, ZigBee, Body Area Network, etc.

Body Area Network (BAN)—in the scope of this invention is a network of sensors attached to the user body communicating over wireless interface.

Motion Monitoring System—in the scope of this invention is a system able to collect various instantaneous vectors such as: acceleration, angular orientation, geo-location and orientation, then using various mathematical operations to provide visual representation of the user's motion.

Ski Equipment—in the context of this invention, is any part of equipment used by the skier, such as: skis, ski boots, ski poles, ski clothing, ski glows, etc.

Equipment Parameters—in the context of this invention, is ski or snowboard design and manufacturing parameters, such as: length, weight, toe/center/tail, stiffness, etc. are extracted after manufacturing and entered into application.

Turn Symmetry—in the context of this invention the level of correlation between pressure levels and locations of the COF applied during the left and right turn.

User Parameters—in the context of this invention, is user's physical parameters, such as: weight, height, skiing competence level, etc. entered by the user into the application using mobile terminal user (UI) interface.

Software Program—the term "software program" is intended to have the full breadth of its ordinary meaning, and includes any type of program instructions, code, script and/or data, or combinations thereof, that may be stored in a memory medium and executed by a processor. Exemplary software programs include programs written in text-based programming languages, such as C, C++, Visual C, Java, assembly language, etc.; graphical programs (programs written in graphical programming languages); assembly language programs; programs that have been compiled to machine language; scripts; and other types of executable software. A software program may comprise two or more software programs that interoperate in some manner.

Topological Information—in the context of this invention, information about the topology of the ski slop obtained through any combination of techniques such as: topography maps, GPS, Radio-Telemetry, barometric pressure monitoring, etc.

User—in the context of this invention, person actively using haptic feedback system.

Center of Pressure (COP)—in the context of this invention is a point location of the vertical ground reaction force vector. It presents a weighted average of all pressures over the surface of the foot that is in contact with the ground.

Center of Mass (COM)—in the context of this invention is a point equivalent of the total body mass in the global reference system and weighted average of the COM of each body segment in 3Dimensional space.

Center of Force (COF)—in the context of this invention a point location of a force applied by skier's foot to the insole surface when the whole ski lies flat and in contact with the snow surface reaction force. Said force location is calculated from pressure data obtained from sensors located inside the skiboot insole and reflect neutral control of ankle muscle.

Cloud Server—in the context of this invention is a computing equipment allowing a client application software to be operated using Internet enable devices.

Accelerometer—in the context of this invention is an inertia based device measuring acceleration component based on device motion and gravity.

Gyroscope—in the context of this invention is a sensor to measure an angular rate of change in device orientation irrespective to gravity.

Magnetometer—in the context of this invention is a sensor to measure magnetic field by computing the angle of the Earth magnetic field and comparing that measurement to the gravity measured by an accelerometer.

Pressure Sensor—Atmospheric—in the context of this invention is a sensor measuring the differential or absolute atmospheric pressure and used to track vertical motion.

Force Sensor—in the context of this invention is a sensor (resistive, capacitive, etc.), used to measure pressure (in Netwons) of a foot on the insole of the skiboot.

Rotation Vector—Angular Velocity—in the context of this invention is a vector quantity whose magnitude is proportional to the amount or speed of a rotation, and whose direction is perpendicular to the plane of that rotation.

Rotation Matrix—in the context of this invention is a matrix that is used to represent rotation in Euclidean space and to describe device orientation.

Gravity—in the context of this invention is Earth's gravity measured in $m/s^2$ and excluding acceleration caused by the user and consisting of a relative angle between device and gravity vector.

Orientation (attitude)—in the context of this invention is an orientation of the device expressed in Euler angles, rotation matrix or quaternion.

Motion Sensor Fusion—in the context of this invention is a method to derive a single estimate of device orientation and position by combining data from multiplicity of sensors.

Global Coordinate System—in the context of this invention is a x/y/z coordination system referenced to the earth magnetic field and in angle of inclination dependent on geographical location.

Local Coordinate System—in the context of this invention is a x/y/z coordinate of the motion sensor located skiboot, where the x-axis is a horizontal and points to the toe of the skiboot, the y-axis is a horizontal and points to the left and the z-axis is vertical and points up.

Euler Angles—in the context of this invention is a three angles introduced by Loenard Euler to describe orientation of a rigid object using sequence of three consecutive rotations.

Quaternion—in the context of this invention is a mathematical expression used to calculate rotation state of the device using the axis and angle of rotation.

DESCRIPTION OF PREFERRED EMBODIMENT

This embodiment comprises a skiboot (or ice-skate boot) insole configured to measure distribution of forces transmitted to the skiboot insole during downhill run, a 3D motion processing element, a linear resonant actuator to provide feedback to the skier's foot and a wireless personal are network (PAN) transceiver—such as: Bluetooth, ANT, etc., communicating force and motion data to the smart-phone based application. Based on the knowledge of skiing biomechanics, and the information received from the skiboot insole, the smart-phone based application predicts the intended ski trajectory, then provides haptic feedback to the foot of the skier, suggesting proper distribution of pressure points on the insole. Furthermore, the smart-phone application transmits the pressure and motion data obtained form the skiboot insole together with the GPS timing and coordinates to the remote location for post-processing using wireless cellular network. During post-processing, a 3D map based on GPS coordinates is retrieved and superimposed on the motion/pressure data, which may be provided in real-time on a remote computer or a smart-phone. Alternatively, post-processed data may be stored on the remote server and retrieved later by the user.

The insole of the present invention comprises several Microelectromechanical (MEMS) motion processor, providing capability of measuring motion in 10-degree of freedom. Said capabilities are enabled by integrating a 3-axis accelerometer, a 3-axis gyroscope, a 3-axis magnetometer (compass), and a barometric pressure sensor, then process the vectors obtained from said sensors by one of well known motion fusion algorithms. In addition, to motion processing, two or more force pressure sensors are also embedded in the sole, said pressure sensors record the force applied to the pressure point on the insole. When the change in distribution—migration of the center of force (COF), is combined with the motion data, we can obtain the phase of the turn the skis are in, then scaling such results by user and equipment information (weight, height, ski side-cut radius, etc.), provide feedback to the skier's foot indicating timing of change and the amount of pressure necessary to obtain desired turn, while recording said pressure, motion and errors.

Most skiers have an intuitive understanding of skiing, gained from practice and understanding some of the physics behind skiing. Such understanding is useful to skiers of all levels, as it identifies key principles, enabling to properly execute certain movements to improve performance. In general, skiing (downhill), involves high speed run down the sloped terrain using quick turns. The skier gains speed by converting gravitational potential energy into kinetic energy of motion, so the more a skier descends down a heel, the faster he goes. A skier maximizes his speed by minimizing resistance to motion, both from air resistance and snow resistance. While the skier minimizes his air resistance (drag) by reducing his projected frontal area, the reduction of snow resistance requires combination of balance and subtle technique of turn. While the turn is essential to go around objects of gates and arrive safely at the bottom of the slope, the turn itself introduces resistance and as such slows the skier. This is particularly pronounced by less experienced skiers, as they skid around their turns and the skis are tilted on their edge and skis plow into the snow. Also, in some cases, a degree of skidding is unavoidable, more advanced skier, will attempt to carve around the turn using skis natural shape (side-cut), and flexibility. To help in "carving the turn", skier will tilt the skis on the inner edge of the turn, and in general, the larger is the angle between the snow and the ski surface, the tighter the turn is. When the ski is flat on the snow, the radius of the carved turn $R_T$ equals the side-cut radius $R_{sc}$, and the ski turns without skid as it travels in the same direction as its velocity.

However, skid is an important technique used to suddenly change direction, slow the speed or even stop. And unlike carving where a skier eases into the turn, a skidded turn is initiated by simultaneously tilting the edge of skis into the snow and pivoting in the direction of the turn. This results in turning in that direction, due to the plowing effect, since the skis are pointed in a direction that is different from the initial velocity. The steering angle determines sharp is the turn, and the loss of velocity. A steering angle of zero results in the skier moving in a straight line with no turning and no slowing down. A steering angle of 90° results in the skier slowing down with no turning, since the force of the snow plowing into skis without sideway component necessary for turn.

By measuring motion of the foot with 9-degree or 10-degree of freedom, one can monitor motion in 3D, then using knowledge of skier and ski physical parameters predict the progress of motion by extrapolation.

In general, downhill skiing comprise straight skiing with a flat skis between two consecutive turns, and the intrinsic skill necessary for skiing is the maintenance of balance. Balance is maintained by the skier's foot, which through numerous joints, tendons, muscles provides receptive field for two main balance metrics—Center of Mass (COM) and Center of Pressure (COP). In this context, the process of skiing may be divided into three phases: $1^{st}$—initiate transition of balance (initiate turn); $2^{nd}$—ski flat (flat ski between turns); $3^{rd}$—rotate pelvic (start next turn). All these phases are initiated and maintained through changes in the distribution of foot COP and application of said pressure to the skiboot through the skiboot insole.

Without much generalization, it is possible to say that the COP during the turn is located on the outside foot of the turn, while during the flat ski phase (between turns), it is distributed evenly between both feet and the net COP lies somewhere between the two feet depending on the relative weight taken by each foot. Furthermore, we may say that the location of COP under each foot is a direct reflection of the neural control of the ankle muscles. The location of COP under each foot is a direct reflection of the neural control of the ankle muscles. Any movement that flexes the foot or toes downward toward the sole (plantar flexion), will move the COP toward back of the foot, while movement of the foot in upward direction (dorsiflexion), will move COP toward the front of the foot, the movement of foot inward (invertor), moves COP towards the outside of the foot.

The position of COP can be obtained by placing two or more pressure sensors in the skiboot sole, then synchronizing the changes in COP with the motion vectors obtained from the 3D motion monitor. The knowledge of place the COP is at the present time combined with the knowledge of past trajectory, present orientation in 3D space, motion vectors and the location of COP allows prediction of the future ski trajectory. Such trajectory may be changed or influenced by the change in pressure applied to the foot—thus influencing change of COP and in turn change of turn parameters. Such "advise" about the timing and need to change location of COP can be provided through feedback to the skier foot.

This invention describes a system capable of monitoring motion of the skier foot in relation to the snow, measuring the location and distribution of force—pressure point(s), inside the ski boot and provide haptic feedback to the skier's foot, instructing on the time and direction the center of force (COF) must be moved for the optimal execution of the current turn. Such system comprises a skiboot insole for processing of motion and to provide haptic feedback, a smart-phone based monitoring application communicating with the insole using Bluetooth (or other suitable), personal area network (PAN) wireless technology, and with the cloud based server using cellular wireless technology.

The exemplary system is presented in FIG. 1A. Here an insole 100, of a ski boot 110, with an insole 100, communicates with a monitoring application 300, hosted in a smart-phone 200. The monitoring application 300 pre-processes the motion and pressure data, retrieves a GPS time and coordinates from the smart-phone and sends said data using smart-phone cellular radio interface 221, to the cloud service 500, for further post-processing, while the pre-processed motion and pressure data are used to provide haptic feedback to the actuator located in the insole. Based on GPS coordinates extracted from data, the cloud server retrieves 3D map of the area, then superimposes the graphical and numerical parameters of the run on said 3D map. This map, together with the graphical and numerical parameters of the run may be displayed on the remote computer or viewed on the user smart-phone.

Figure 2:
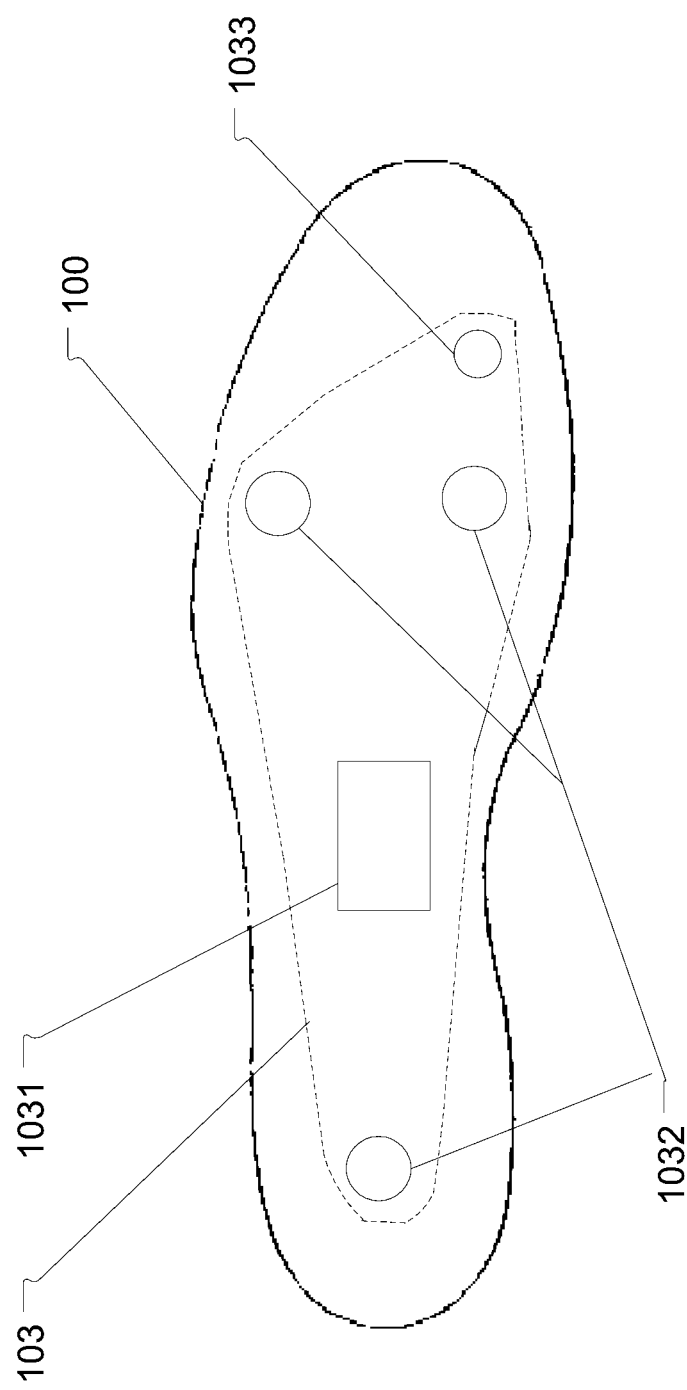
FIG. 2, depicts an innersole and the components of the exemplary haptic feedback system.
Figure 3:
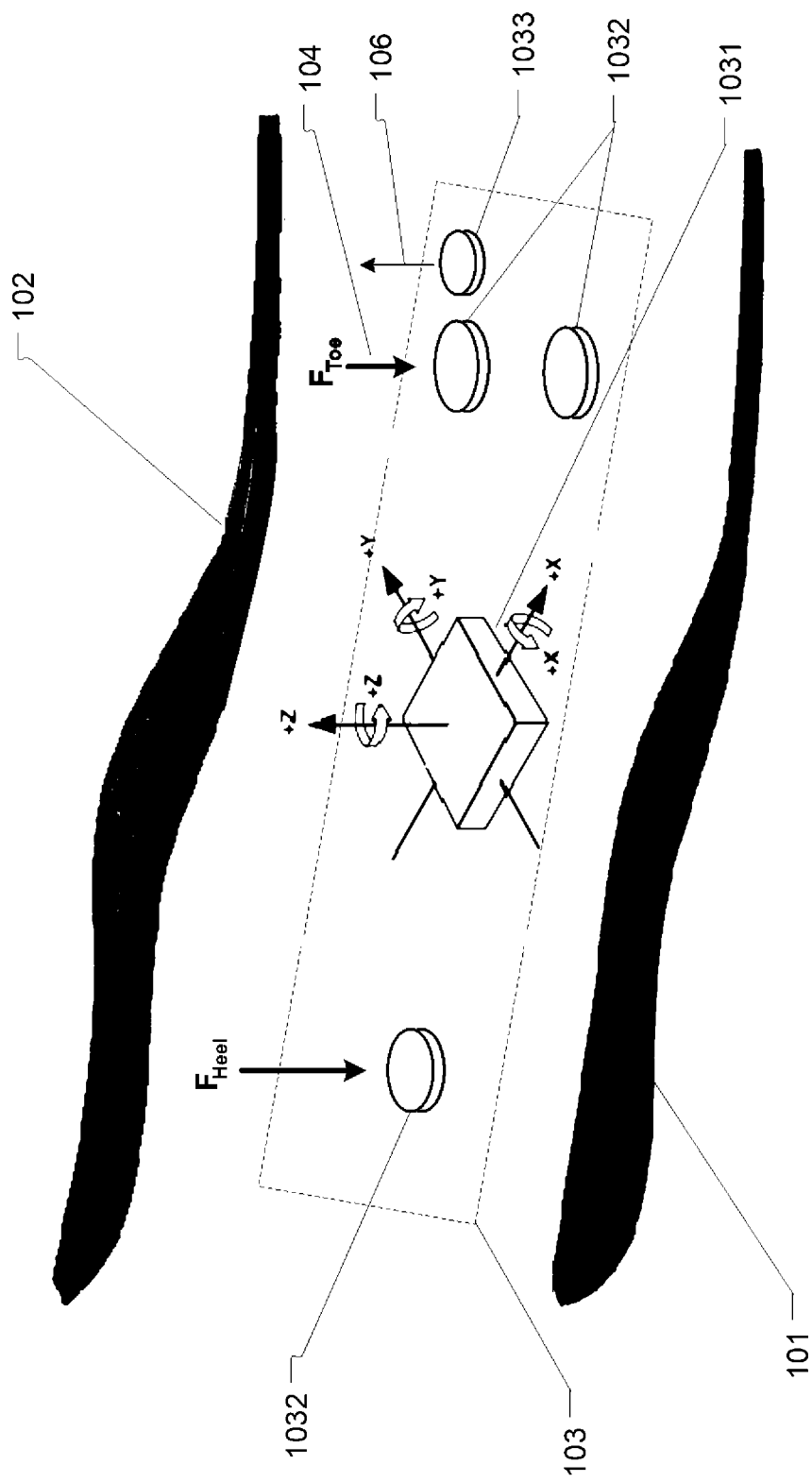
FIG. 3, presents a cross-section of the innersole.

Skiboot insole 100, presented on FIGS. 2 and FIG. 3, comprises of a lower 101, and upper 102, insole surfaces and a motion processing and feedback sub-system 103, sandwiched in between insole surfaces. The motion and feedback sub-system consist of a motion processing element 1031, two or more pressure/force sensors 1032, and a haptic actuator 1033. The motion processing element 1031, is configured for analysis of motion with 10-degree of freedom comprising several inertial MEMS sensors: a 3D gyroscope; a 3D accelerometer; a 3D magnetometer (compass); and an atmospheric pressure sensor.

The 3D gyroscope is used to measure angular rate change by the insole in degrees per second, thus allowing measurement of angle, travel and as such, track changes in the insole orientation (pitch, roll and yaw angles). The accelerometer is used to measure acceleration of the insole caused by motion due to gravity in an X, Y, Z coordinate system by computing the measured angle of the device, compared to gravitational force and the results are expressed in m/s². By integrating acceleration vector a(t) over period of time, we obtain velocity function v(t). The 3D magnetometer measures the earth magnetic field at specific location. By computing the angle of the magnetic field, and comparing that angle to gravity obtained from accelerometer, we are able to determine the orientation of the insole with respect to magnetic North. Beside, sensing the direction of earth magnetic field, magnetometer is used to eliminate drift of gyroscope. Furthermore, the insole motion processing element employs an atmospheric pressure sensor to obtain changes in the altitude and rate of descent by detecting ambient air pressure ($P_{amb}$) according to equation:

$$h_{alt} = (1-(P_{amb}/10132)^{0.190284})*145366.45$$

to track vertical motion.

By observing three-dimensional vector of gravity measured by the accelerometer along with measurements provided by gyroscope, we can determine orientation of the ski (pitch, roll, yaw), while the skier is in motion. Also by subtracting gravity vector form acceleration, we obtain linear acceleration of the ski. The orientation angles describe motion, and are used to provide graphical representation of motion. Furthermore, we derive a rotation vector from results provided by accelerometer, gyroscope and magnetometer. This vector represents a rotation around a specific axis and corresponds to the components of a unit quaternion, which represents yaw, pitch and roll and is used to graphically represent motion of the insole.

The quaternion of the insole (and skiboot), is calculated by, first converting gyroscope angular rate to a quaternion representation:

$$dq(t)/dt=\tfrac{1}{2}\omega(t)*q(t),$$

where $\omega(t)$ is the angular rate of motion and $q(t)$ represents normalized quaternion. Then, we convert the accelerometer results from local coordinate system, represented as $A_L$ to global coordinate system, represented as $A_G$, by using previously obtained quaternion as:

$$A_G(t)=q(t)*A_L(t)+q(t)'.$$

Then calculate acceleration quaternion as:

$$qf(t)=[0\,A_{Gy}(t)\,-A_{Gx}(t)\,0]*\text{gain}$$

which is added as a feedback term to quaternion from gyroscope, then add magnetometer data to the azimuth (yaw) component of the quaternion.

Figure 4:
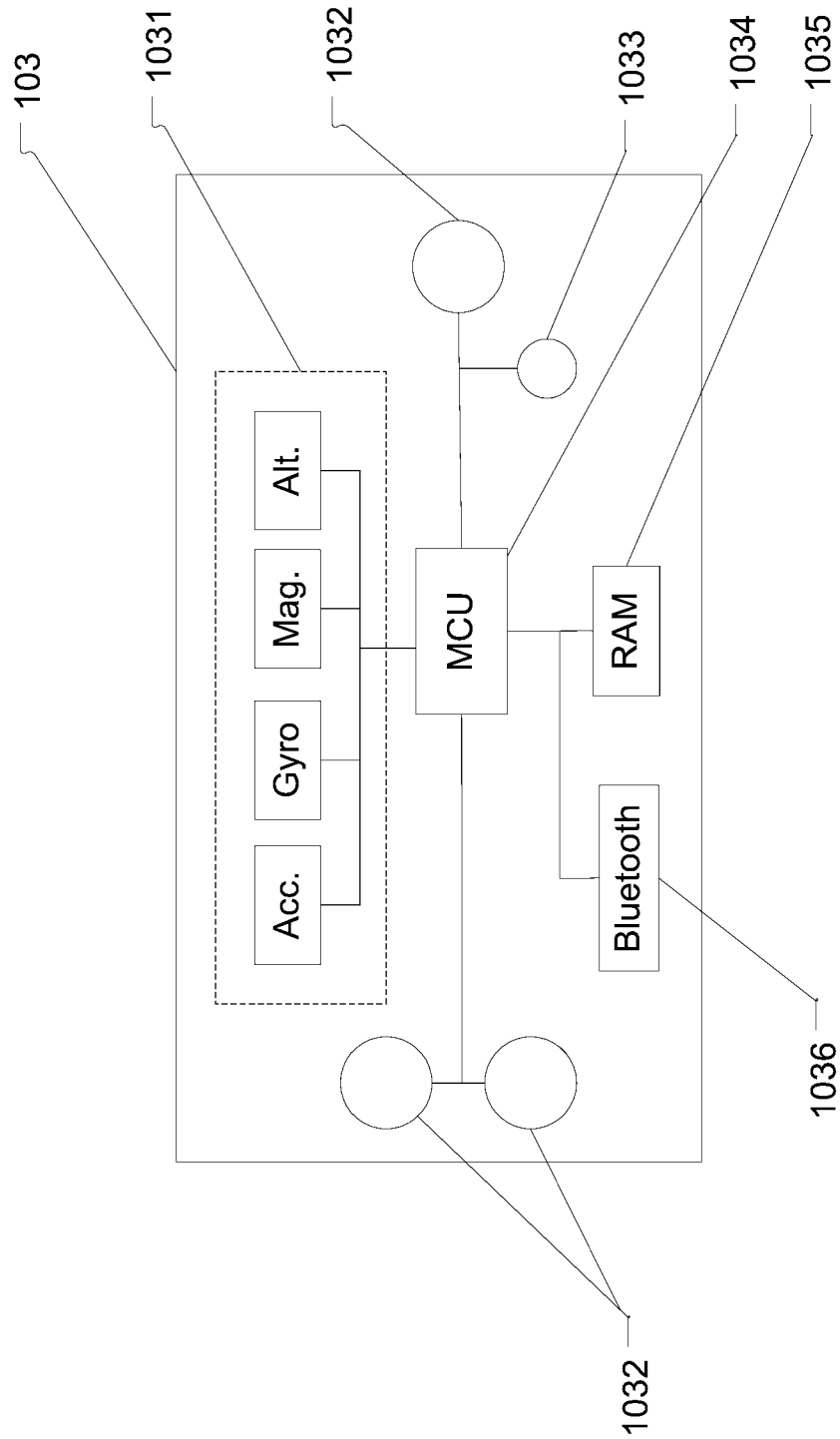
FIG. 4, presents relation between the skier's foot and the components of the skiboot innersole.

The exemplary skiboot insole motion processing and feedback sub-system 103, is presented in FIG. 4, and comprises of: a motion processing element 1031, comprising a 3-axis accelerometer, a 3-axis gyroscope, a 3-axis magnetometer and a barometric pressure sensor. In addition, the motion processing and feedback sub-system consist of several force pressure sensors 1032, a haptic feedback actuator 1033, a Bluetooth RF interface 1036, and microprocessor 1034 with it's program memory 1035. The sensors within the motion processing element 1031, are connected to the microprocessor 1034 using one of appropriate digital interfaces, such as I2C, or an appropriate analog interface. Similarly, the force pressure sensors may be connected to the microprocessor analog-to-digital (ADC) converter using appropriate analog interface or directly to the microprocessor digital interface, while the haptic feedback actuator may be connected to the microprocessor digital-to-analog (DAC) converter.

Figure 5:
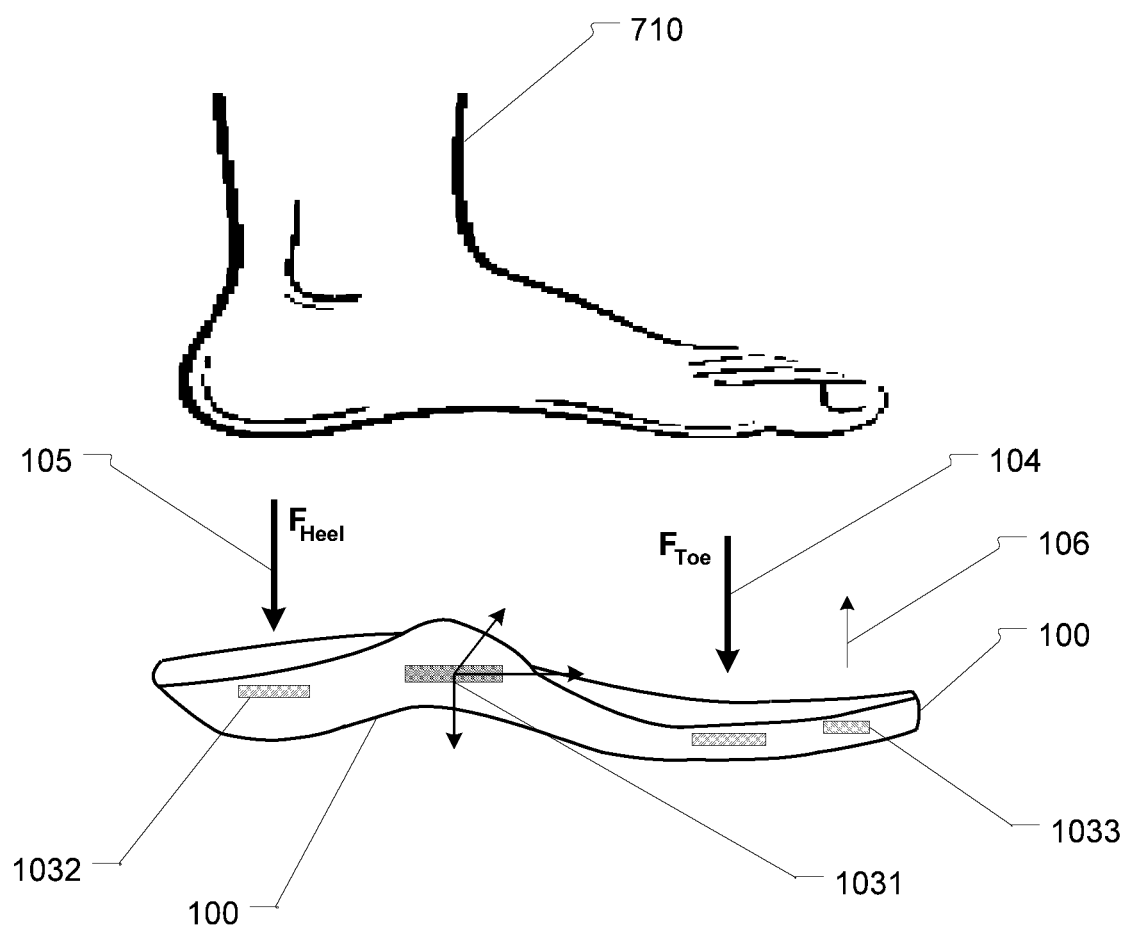
FIG. 5, depicts an exemplary architecture of the haptic system controller.

The relation between skier's foot 710, and the skiboot insole 100, is presented in FIG. 5. During the run, the location of the pressure points to the skiboot/ski and the distribution of pressure (force) between both feet provides the kinetic mechanism necessary to initiate and end a turn. While between turn—frequently referred a 'flat ski', the force is distributed equally between both feet and equally between front and back of the foot, the location of the pressure points between the feet and inside the skiboot changes during the turn. From FIG. 5, one may observe two main location of the force—at the front of the foot ($F_{Toe}$) 104, and the back of the foot ($F_{Heel}$) 105. The actual location of those pressure points and consequently the location of center-of-force (COF) may be measured by two or more force sensors 1032. The haptic feedback 106, to the skier foot is provided by actuator 1033.

Each turn in skiing may be separated into three phases: 1) ski flat phase; 2) start of transition phase; 3) pelvic leg rotation phase. During the ski flat phase, the skier COF is distributed evenly between both skis and located in a neutral point (evenly distributed between toe and heel of the insole). The skier selects inner ski—effectively selecting direction of the turn, and start the transition phase. At this moment, the COF of the inner foot migrates toward the pinky toe and initiated forward movement on the "new" outer ski, this moves the COF of the outer foot toward the big toe. Then enters the third phase by rotating his leg pelvic moving the COF firmly on the outer ski which places the resulting force $F_R$ on the edge of the outer ski.

Figure 6A:
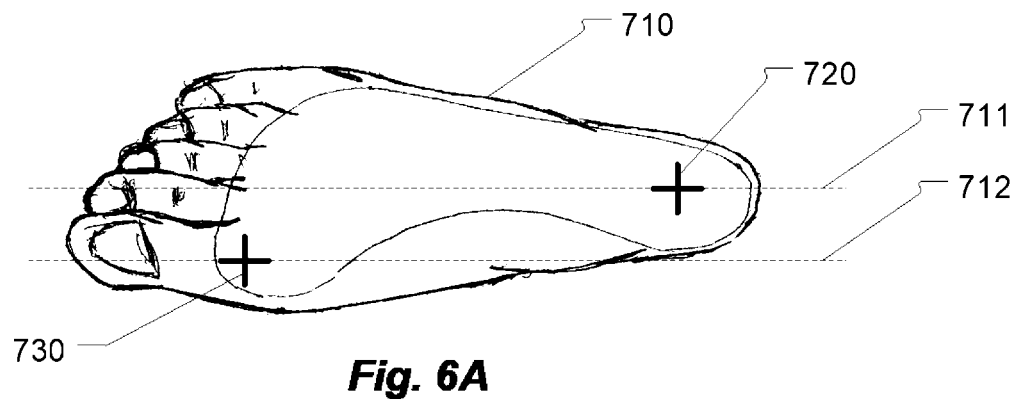
FIG. 6A, presents skier foot bio-mechanical pressure points.

For the outer ski, this process is presented in FIGS. 6A, 6B and 6C and described below. In FIG. 6A, the foot 710, during the flat ski phase between edge change, the pressure is distributed evenly between two main mechanical points 720 located at the heel on the centered axis 711, and on the center of head of the $1^{st}$ metatestral (MT) bone 730, of a foot and centered along the inside edge 712.

Figure 6B:
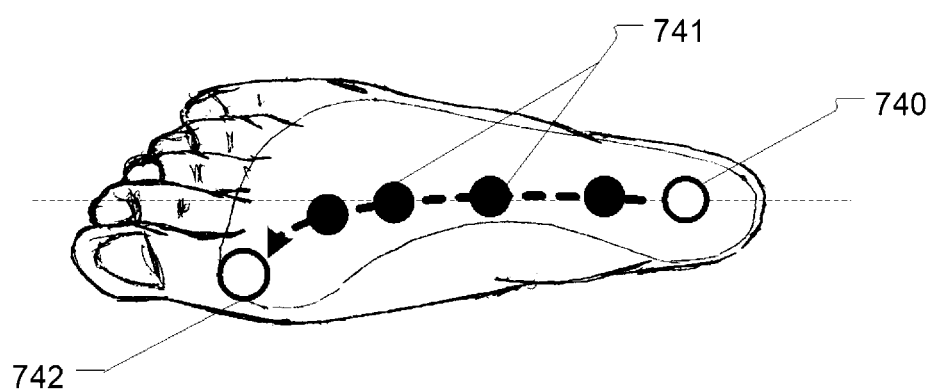
FIG. 6B, presents the center of force (COF) point under the heel and it's forward transition to become center of pressure (COP) in the phase between two consecutive turns.
Figure 6C:
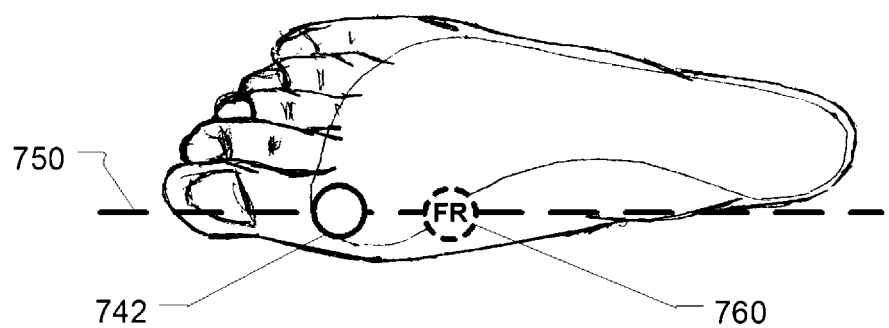
FIG. 6C, presents the COP position at the end of the turn when it lays over the top of the inside ski edge and on the same axis as the center of mass (COM) resulting force ($F_R$)

The start of transition is presented in FIG. 6B, here, when the COF 740 is located under the skier heel and progresses forward to position 742, —the head of the $1^{st}$ MT. The COF essentially "rolls" inwards, the ankle is plantar flexed and the foot is inverted, the leg rotates while COF moves forward along arc 741, towards the head of the first MT. When the head of the first MT is maximally loaded (FIG. 6C), the COF and the skier fully rest on the outer foot (monopedal stance), while the resulting force $F_R$ 760 align with the COF above the edge of the outer ski 750. At this moment, the rolling of the foot inwards generates torque, which is directed into turn.

Figure 7A:
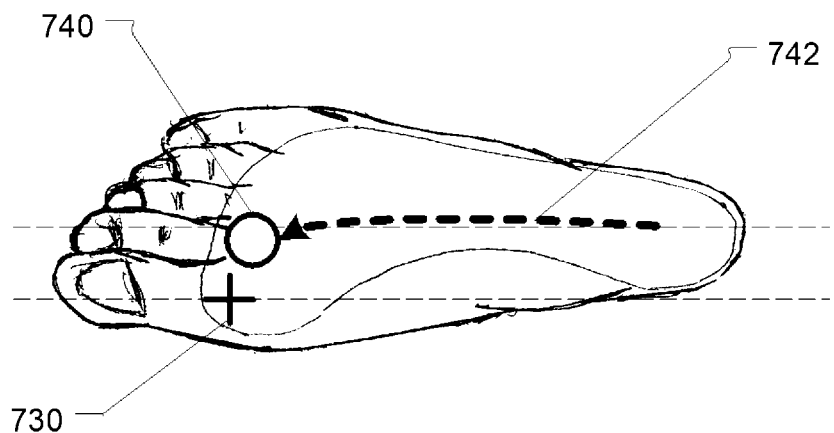
FIG. 7A, presents the incorrect migration of the COF during turn from the foot heel to the head of the second toe.
Figure 7B:
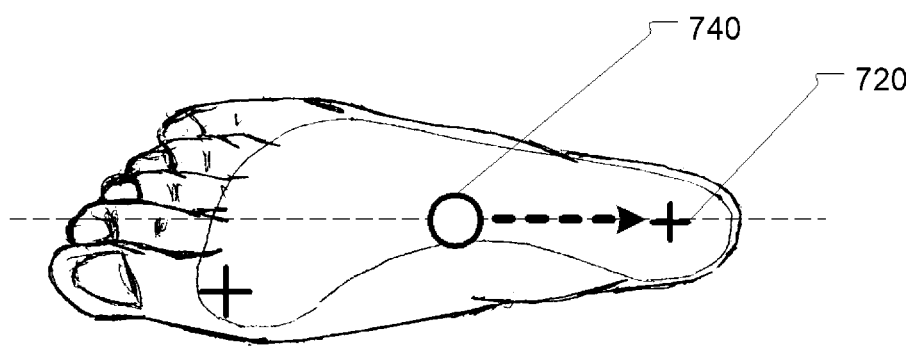
FIG. 7B, presents the migration of the COF back from the incorrectly placed COF to the center of the foot and back to the heel.

When the distribution of pressure between skis or the transition of COF from the heel of the outer foot to the head of $1^{st}$ MT fails, the turn is unsuccessful and skier looses his balance. The graphical representation of such turn is presented in FIGS. 7A and 7B. At some point between the edge change but before the new outside ski attains significant edge angle (without necessary plantar flex of an ankle), a moment develops between the inside edge of the ski and the COF resulting in inversion moment of force. Torque associated with vertical axial rotation of the leg, FIG. 7B, will reverse the movement of the COF 745, to the point of origin 720 as it is aligned with the heel and lower limb. Such reverse can't be stopped and skier looses his balance.

Figure 8:
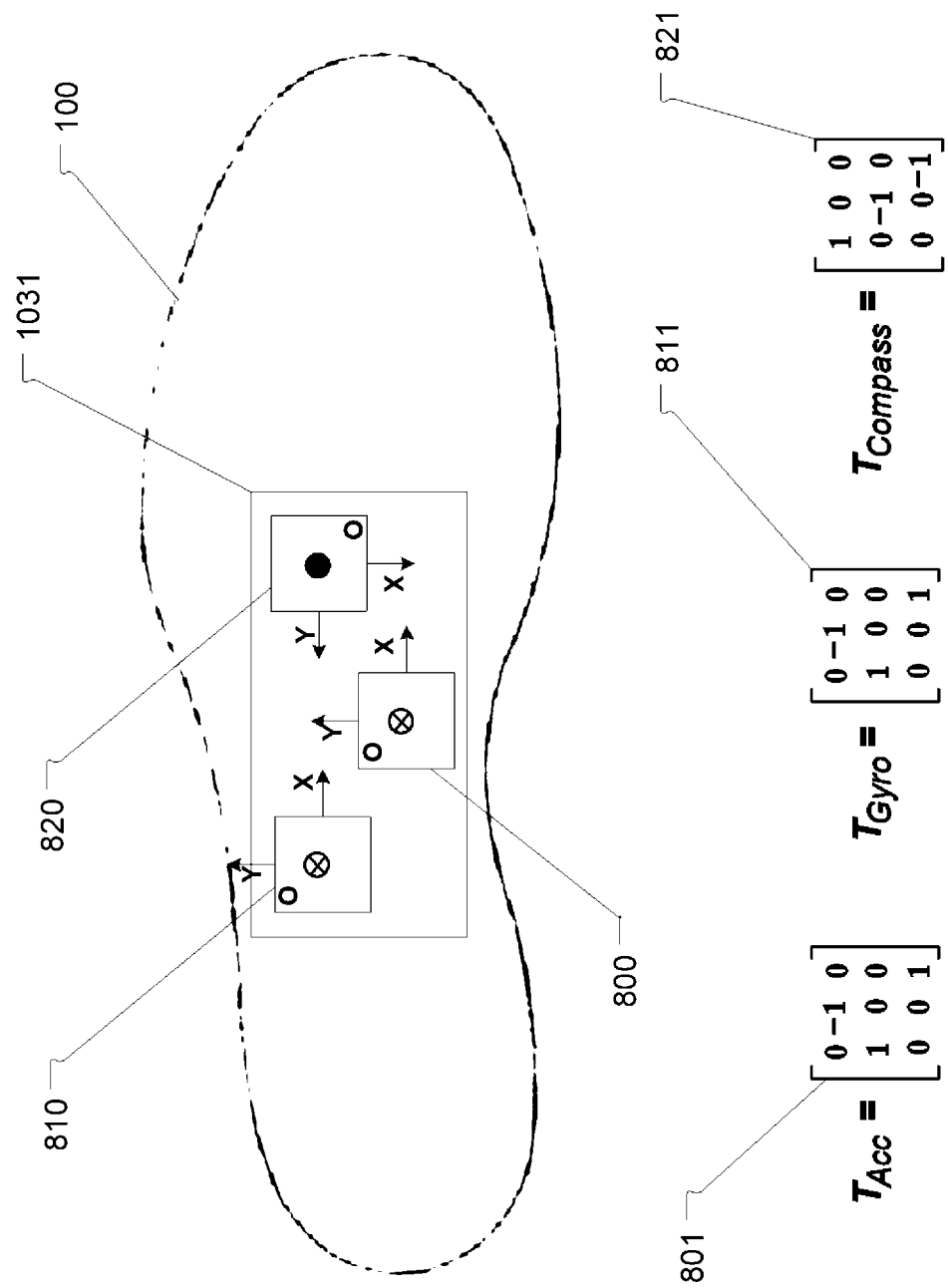
FIG. 8, presents the orientation of the motion sensors (accelerometer, gyroscope, magnetometer), and their transformation matrixes.

An exemplary orientation of motion sensors within the insole and it's relation to their respective matrix is presented in FIG. 8. This relation is important to establish local coordinate system, as the matrix obtained from different sensors will rotate depending on insole orientation in reference to the global coordinate system. The motion processing element 1031, embedded in the skiboot insole 100, and comprises of: 1) an accelerometer 800, which Y axis points to the left side of the insole, the X axis points to the front of the insole and the Z axis points up; 2) a gyroscope 810, which Y axis points to the left side of the insole, the X axis points to the front of the insole and the Z axis points up; and a magnetometer 820, which Y axis points to the back of the insole, the X axis points to the right of the insole and the Z axis points down. Related to this orientation of sensors are respective matrixes: 801, 811 and 812.

Figure 9:
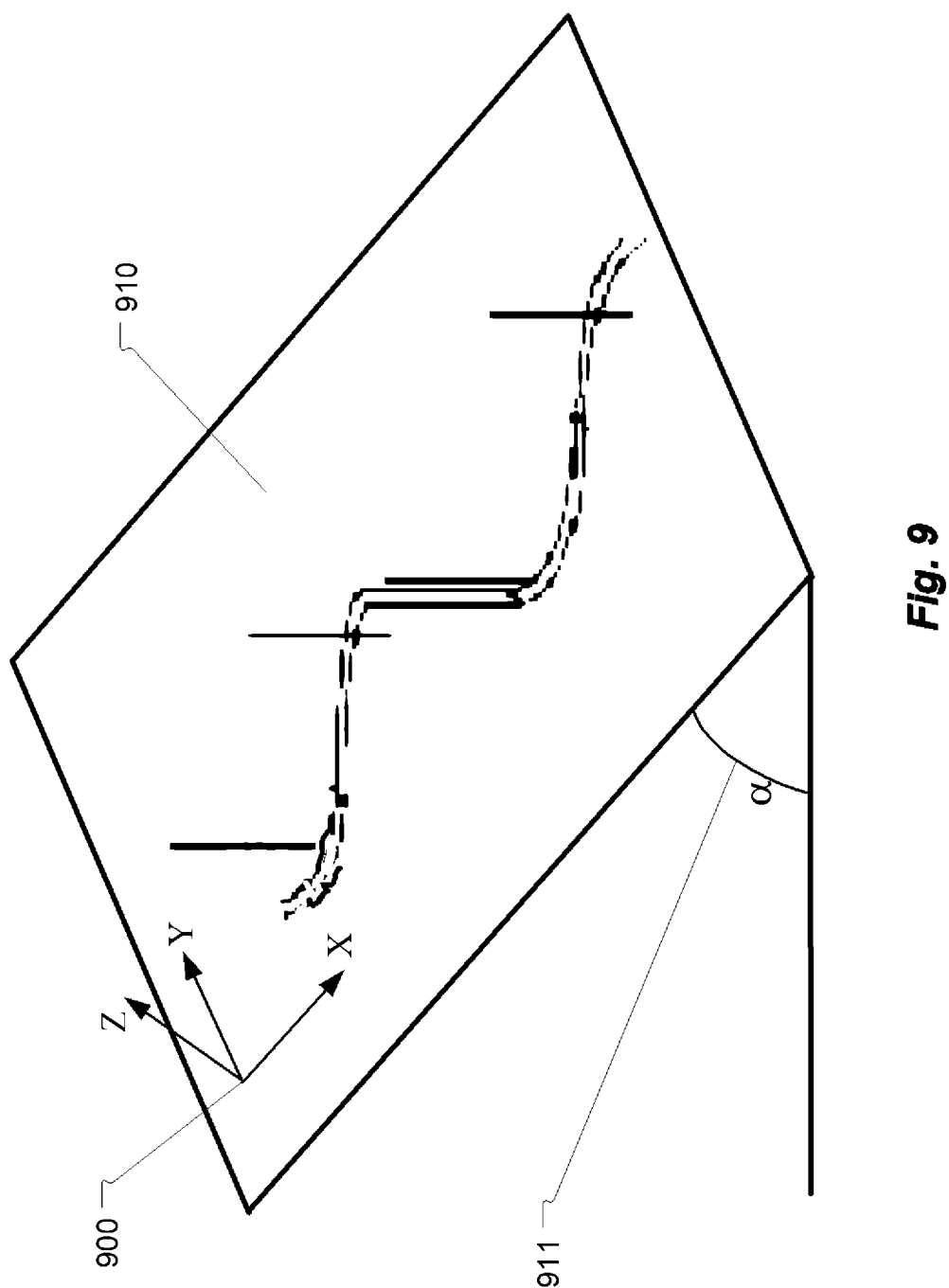
FIG. 9, presents the view of global coordinate system in relation to ski slope.
Figure 10:
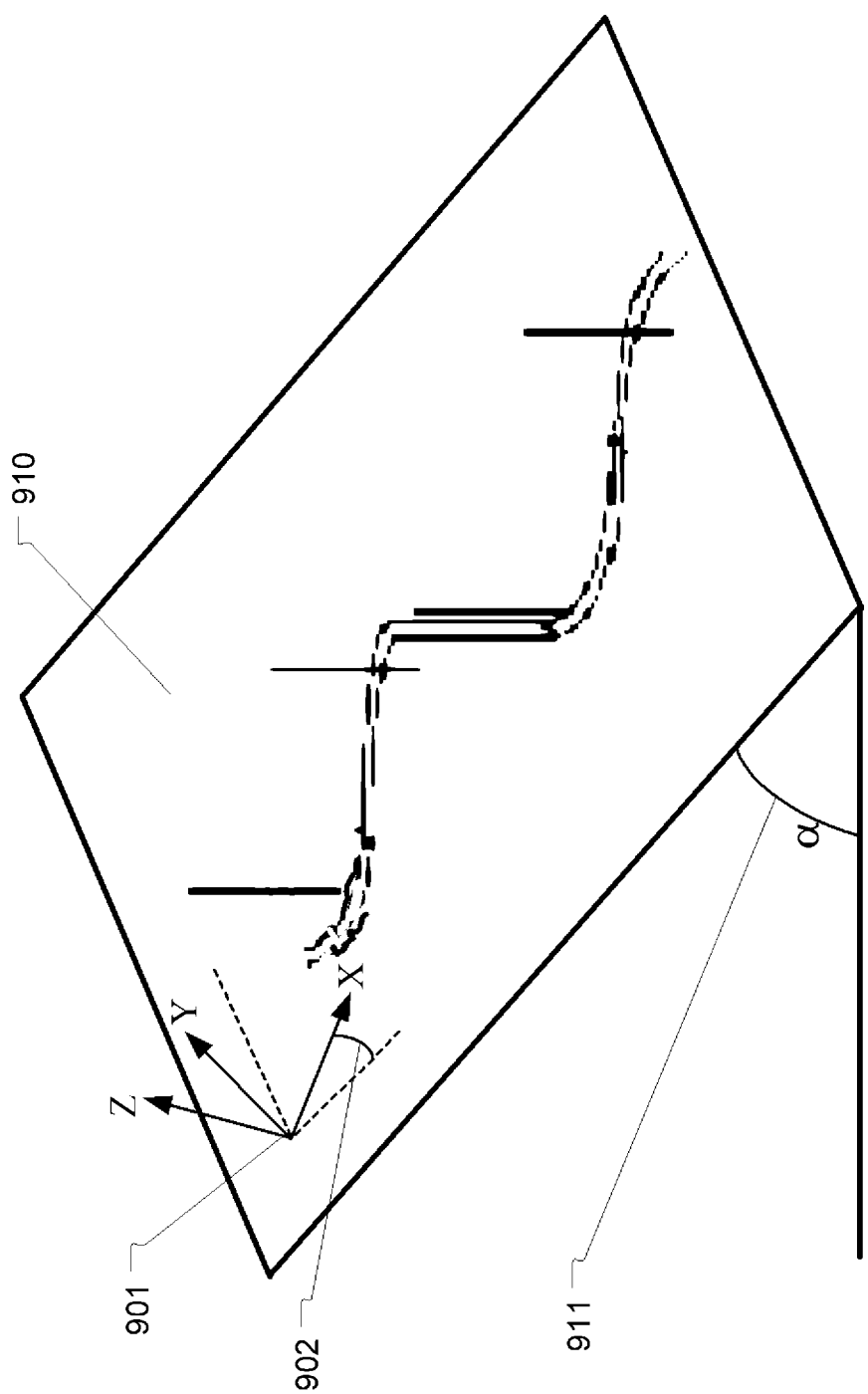
FIG. 10, presents the view of local (skiboot) coordinate system in relation to the ski slope.

The insole global coordinate system is established in reference to the earth magnetic field at the specific geographical location obtained from the magnetometer 820, by comparing it's angle to gravity measured by accelerometer. The orientation of the global coordinate system 900, to the slope 910, with an incline a 911, is presented in the FIG. 9. Here, the Z axis is perpendicular to the ground and the negative Z points in direction of earth gravity. The X axis points to East and the Y axis points to magnetic North. After the global coordinate system is established, the local coordinate system 901 in FIG. 10, a coordinate system of the insole in relation to the global coordinate system may be calculated by reading measurement form accelerometer and gyroscope.

Figure 11:
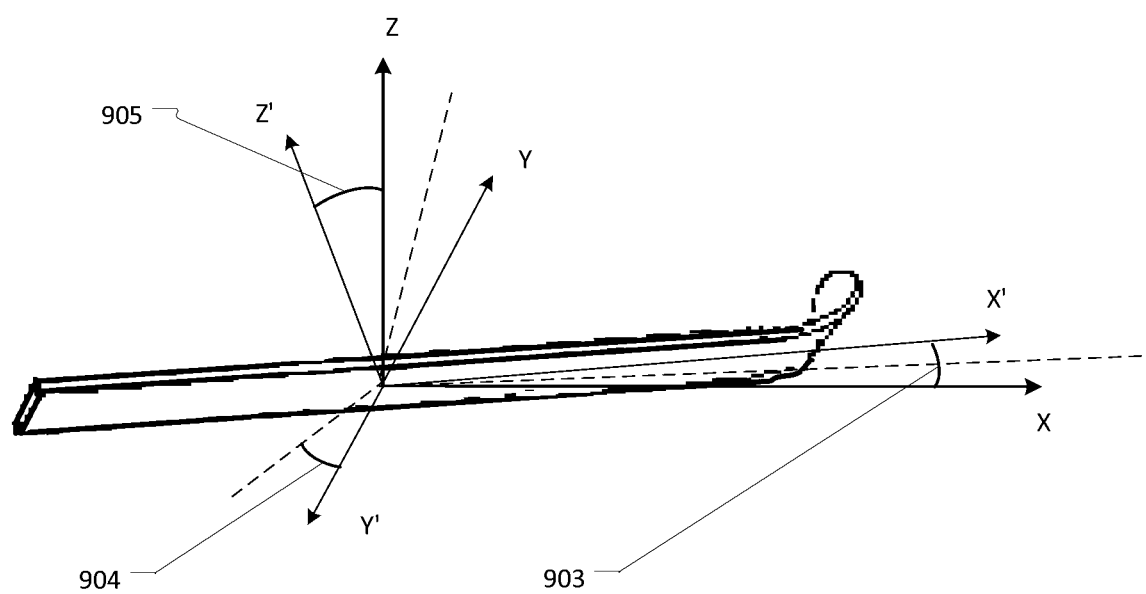
FIG. 11, presents transformation of local coordinate system during turn.

The method of presenting motion and orientation of the insole and by extension ski in the 3D space can be explained based on FIG. 11 and the processing allowing visualization of said motion described in the following sections. Here at time $t_0$, the ski is flat and with the X axis pointing horizontally in the direction of slope line. The Y axis points to the left, while the Z axis point upward. After start of transition, at time $t_1$, ski rotates along the Z axis by angle $\Psi$ (yaw), 905, and along the X axis by angle $\theta$ (pitch), 903, and along the Y axis by angle $\Phi$ (roll), 904, into left turn. This motion may be described in terms of Euler Angles using Euler motion theorem as three consecutive rotations of coordinate system xyz$\Rightarrow$x'''y'''z'''$\Rightarrow$x''y''z''$\Rightarrow$x'y'z', where the $1^{st}$ rotation is along the z-axis, $2^{nd}$ rotation is along the former x-axis and $3^{rd}$ rotation is along the former y-axis.

The insole orientation may also be described in terms of matrix rotation. For a 3D matrix the rotation $\theta$ (pitch), may be described as:

$$R_\theta = \begin{bmatrix} \cos\theta & -\sin\theta & 0 \\ \sin\theta & \cos\theta & 0 \\ 0 & 0 & 1 \end{bmatrix}$$

so the vector $V_0=[1,2,0]^T$ will become v'-[cos $\theta$, sin $\theta$, 0]$^T$. As the rotation matrix are orthogonal with detriment 1 and with own transpose and an inverse, the rotation matrix will reverse its rotation when multiplied with the rotation inverse. We can also use the matrix rotation to obtain direction of earth gravity in relation to orientation of the insole. When the insole change orientation, its Z axis moves from z to z' by rotation matrix A, according to: z'=A*z. As for the local (insole) coordinate system the z' vector is $[0,0,1]^T$, the vector z is obtained by the inverse of rotation matrix.

Rather then use computationally intensive matrix rotation to obtain insole orientation, we may use mathematical expression of quaternion to calculate insole rotation state according to Euler's rotation theorem stating that device orientation may be expressed as rotation about one or more axis. This axis representing unit vector magnitude and angle remains unchanged—except for the sign, which is determined by the sign of the rotation axis represented as three-dimensional unit vector $\hat{e}=[e_x,e_y,e_z]^T$, and the angle by a scalar a.

Calculation of quaternion requires only four terms when the axis and angle of rotation is provided. Quaternion extends complex numbers from two-dimensions to four-dimensions by introducing two more roots of −1 as:

$$i^2=j^2=k^2=ijk=-1$$

which are then multiplied with real components as:

$$r+ix+jy+kz$$

then conjugate and normalize to arrive with unity |u|=1, or quaternion.

Figure 12:
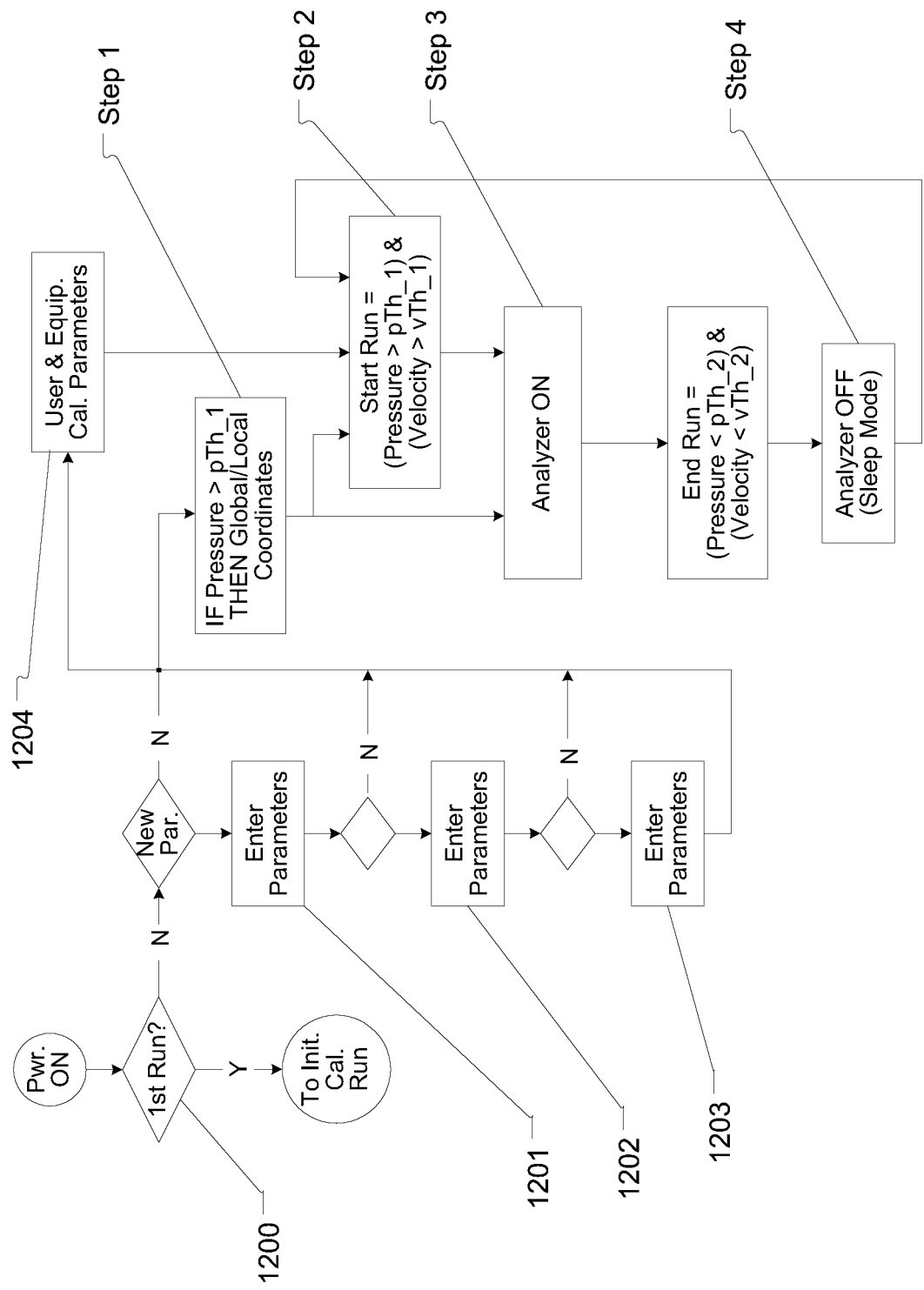
FIG. 12, presents a control process of the haptic feedback system.
Figure 13:
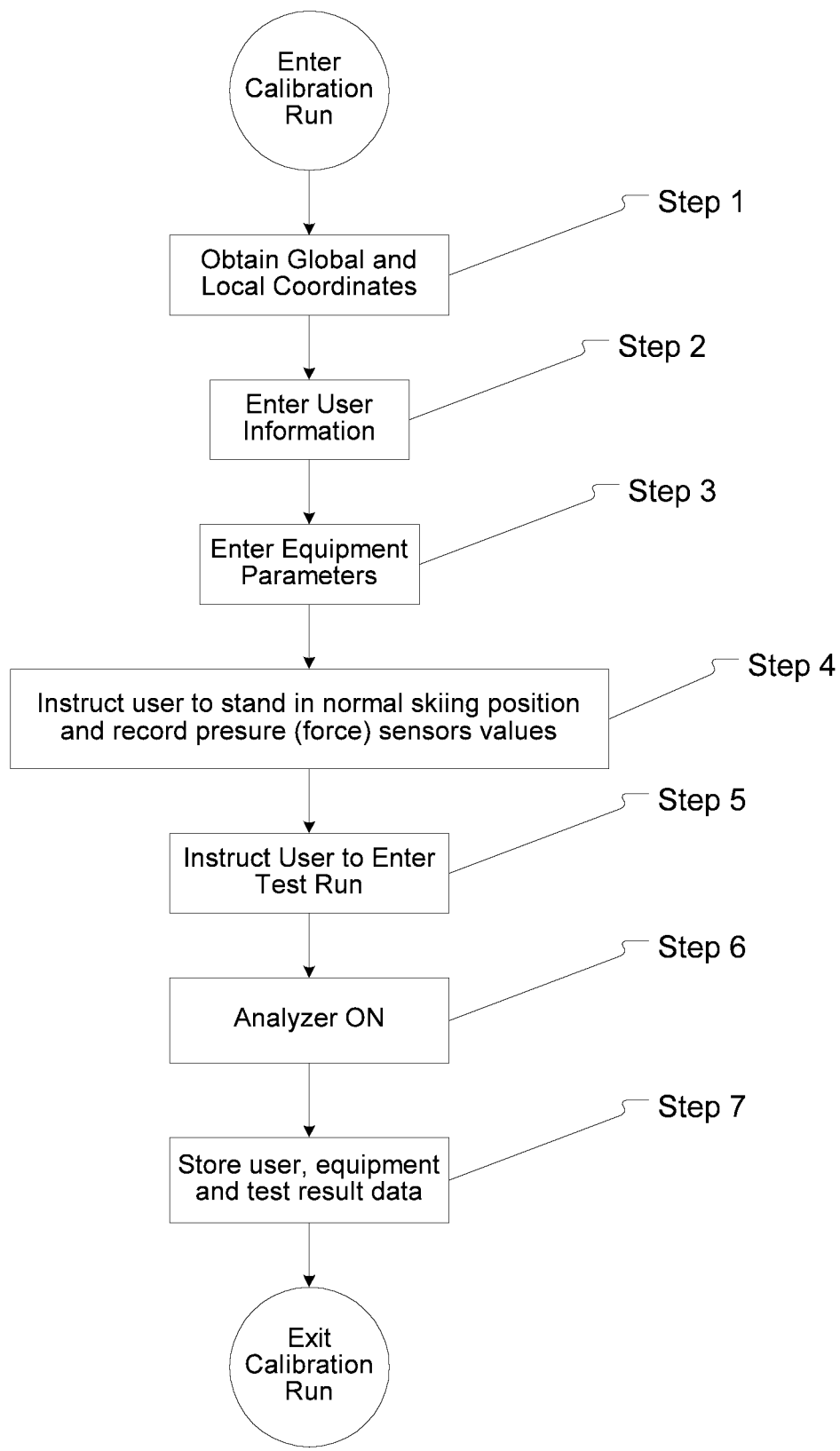
FIG. 13 presents the flow of the haptic system initial calibration.

Operations and procedures of said system is presented in FIGS. 12 and 13 and described in details in the following sections. In FIG. 12, upon initial power-up and association of the insole Bluetooth transceivers with the application, the system control program checks if this is $1^{st}$ run 1200, indicating the initial calibration procedure was executed. Depending on user parameters, such calibration may be performed during the first run of the day, or at the request by the user, to allow for adjustments to the changing snow conditions, etc. If this is the $1^{st}$ run, application enters the initial calibration routine of FIG. 13, otherwise, user is given an option to update through the smart-phone user interface (UI), to update one or all system parameters. If said option is rejected, application enters the main control loop, otherwise, the user is prompted to select which information—first (user parameters), second (equipment parameters), or third (snow condition parameters).

The First information 1201, comprises of user parameters consisting among the others: body weight; height; and skiing proficiency level—"beginner", "intermediate", "advanced", "professional".

The Second information 1202, comprises technical parameters of the user equipment, consisting among the others: length of the ski; ski natural turn radius (side-cut); etc.

The Third information 1203, comprises the snow conditions present during the calibration run, such as: "groomed slope", "icy", "powder". This information is used to derive two coefficients—first, to scale the time between the start of transition and when the COF reaches position 742 (FIG. 6B); second, to scale the distribution of COF between inner and outer ski.

The second and third information may be entered by the user manually or scanned to the application from the QR-code or NFC parameter tag attached to the equipment.

The initial calibration procedures comprises of 8 steps which are described in FIG. 13, and in the following paragraphs.

In Step 1, user is instructed to enter his physical parameters, such as weight, which is used to calculate the distribution of force between both skis using Newton's Second Law as well as calculating distribution of force inside the skiboot.

In Step 2, user enters equipment parameters by either scanning a QR-code or a NFC tag attached to the equipment or manually using smart-phone UI. Among the others, some of parameters like the length and the turning radius or, side-cat of the ski are important factors used in conjunction with motion vectors to calculate the ski effective turning and derive an optimal turning radius during turns.

In Step 3, user enters the current snow condition of the slope. This is used to appropriate scale the pressure point (weight) distribution and timing of COF change in different condition of the slope, for example change of technique between powder skiing and skiing on icy snow.

In Step 4, application instructs the user to step into the skis and reads data from motion sensors for the purpose of establishing global and local coordinate system, then in Step 5 instructs the user to perform several exercises:
1) Stand in normal, relaxed bi-pedal position with body weight equally distributed between both skis, then record the force [N], measured by each pressure force sensor;
2) Stand in a crouching position, leaning forward and elbows resting on the knees, then record the force [N], measured by each pressure force sensor;
3) With both skis parallel and without support of the ski poll, bend knees and push inward (as during sharp turn with both skis on the edge), then record the force [N], measured by each pressure force sensor;

4) Instruct user to make a run consisting at least four carved turns. Allow for the ski to accelerate by ignoring first two turn, then record motion parameters during two consecutive turns;

5) End calibration procedure.

After power ON, the MCU 1034, enters standby mode and remains in said mode until an interrupt from the insole pressure sensor is above threshold pTh_1, indicating both of user feet are in the skiboot and on the ground. If new calibration is not required, system enters normal operation, FIG. 12, Step 1, obtains global and local coordinate system, then enters Step 2. In Step 2, system starts monitoring motion, and if the velocity exceeds threshold vTh_1, indicating start of the run, enters into Step 3, then start sending motion and forces data to the smart-phone application over radio interface 211. System remains in State 3, until velocity of the system is above threshold vTh_2 and the pressure force measurement is above threshold pTh_2. When the velocity is below threshold vTh_2 and pressure forces is below threshold pTh_2, indicating end of day (skiboot off), or time-brake in skiing (lift, rest, etc.), system enters Step 4, stops processing of motion and forces, forces radio interface transceiver 1036, into power OFF mode and MCU 1034, into a standby mode—thus conserving power consumption of the system. After exiting Step 4, system remains in the sleep mode until condition of Step 2—pressure force above pTh_1 and velocity above vTh_1 conditions are not satisfied.

The motion and pressure force data received from the insole 100, by the smart-phone 200, is processed by application 300 to provide user with the haptic feedback. Based on signal from sensors, using inertia navigation algorithms, application calculates kinematics of the ski trajectory. Then using user parameters, creates biomechanical model of foot/ski interface, and the sensor kinematics is translated to segments kinematics by measuring the position (and timing) of COF. Such calculation provides two results: one, current ski trajectory; two, prediction of future trajectory in relation to the local coordinate system and location of COF. The first set of results are sent to the cloud based server 500 for further processing using smart-phone cellular radio interface 221, while the second sets of results is used to provide corrective feedback to the user foot.

This corrective feedback is in form of haptic pulses applied by the haptic actuator to the big toe of the foot. This feedback provides information of timing, direction and destination of the COF necessary to successfully start and finish turn. This feedback may be coded in various ways, for example, different frequency and/or force during different phases on turn, etc.

Figure 17:
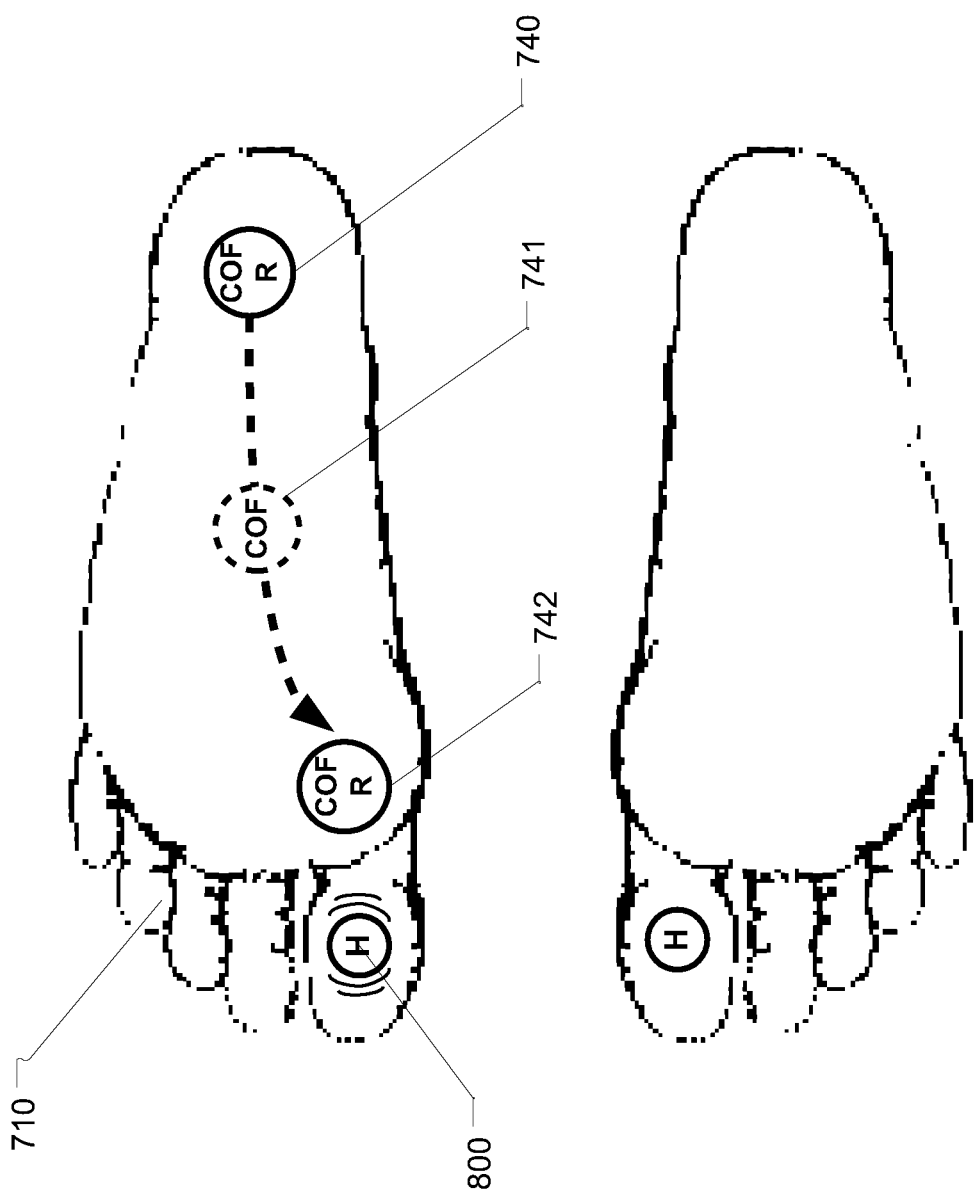
FIG. 17, presents operation of haptic feedback actuator on the outside foot during the transition into left turn.

Operation of said haptic feedback is presented in FIG. 17. Here we see the outside (of the turn) foot 710, right after start of transition, which the haptic feedback actuator 800, vibrating at high frequency (or force), when the COF is still located under skier heel, indicating time to transition on the outside ski and move COF to the base of $1^{st}$ MT. The vibration frequency may decrease while COF moves forward to new position 741, and completely stop when the COF reaches the desired position 742, while never stop vibrating at high frequency when the COF fails to reach the base of $1^{st}$ MT.

Together with the first set of results, application sends to the cloud server GPS coordinates and timing. The first set of data is then used to generate a numerical and graphical presentation of the run. An exemplary representation of run data is presented in FIGS. 14, 15 and 16. Such run data may be retrieved form the cloud server later by the user and displayed on the user smart-phone (for example during the travel on the lift), or in real-time on a remote computer. Furthermore, using the GPS coordinates, cloud server may superimpose said data on 3D map of the terrain, giving additional reference and meaning to the data.

Figure 14:
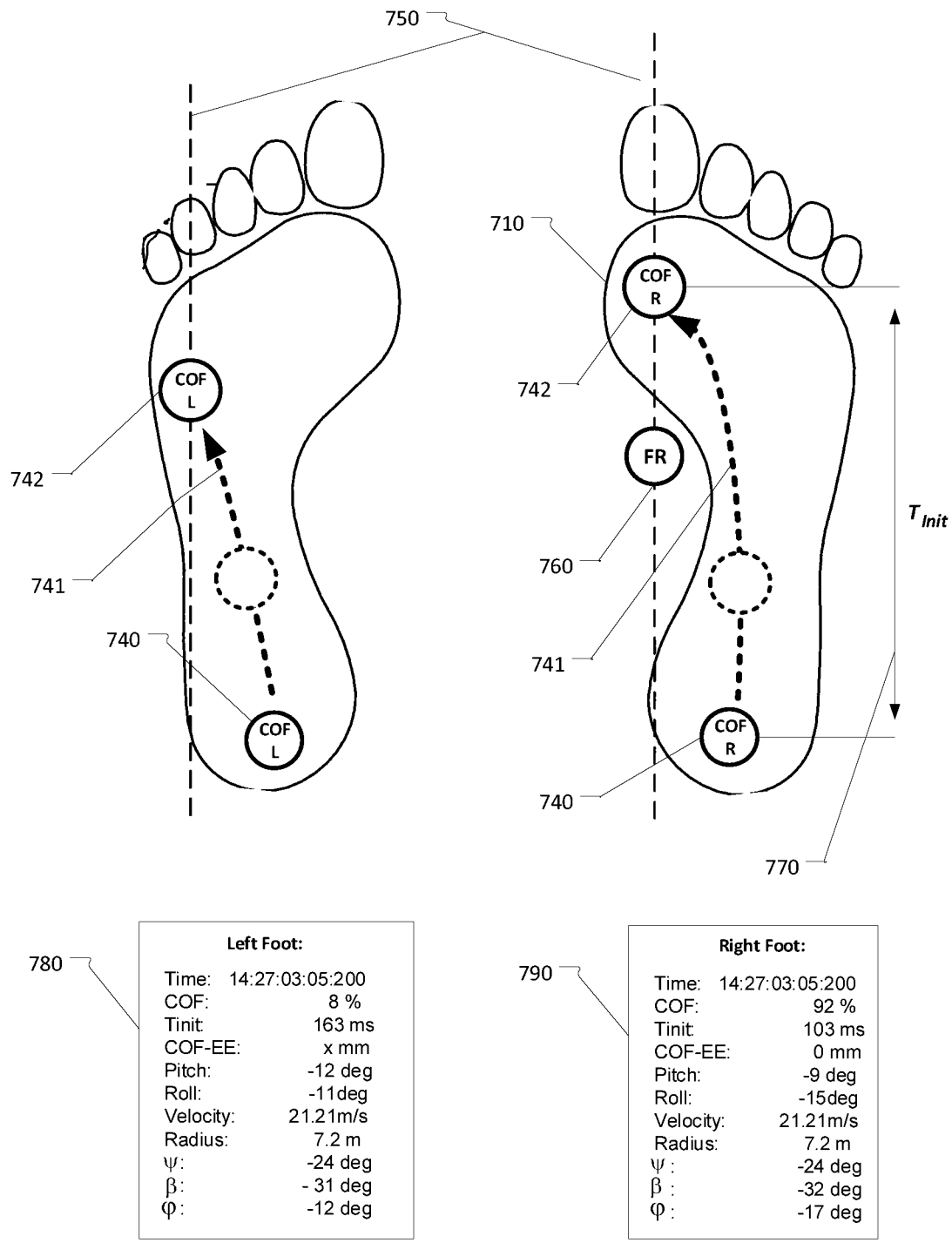
FIG. 14, presents graphical and numerical representation of motion and pressure points transmitted to the skiboot insole by the foot during a successful turn.

After the post-processing of first set of results by the remote cloud server, visual and numerical representation of the run can be displayed on a remote computer or on a smart-phone. Among the others visual presentation possible, some of the visual options are presented in FIGS. 14, 15a 16. FIG. 14, shows left and right foot with a graphical representation of the location of COF and 3D motion parameters in relation to the GPS time. Here we see the movement of the COF 740 from the start of transition into the left turn, the location of the COF 742 after the initial phase of the turn and the time (in milliseconds), of the transition 770. Furthermore, the calculated location of the resulting force $F_R$ 760, a point where the skier center of mass (COM) is acting on the ski and snow.

Figure 15:
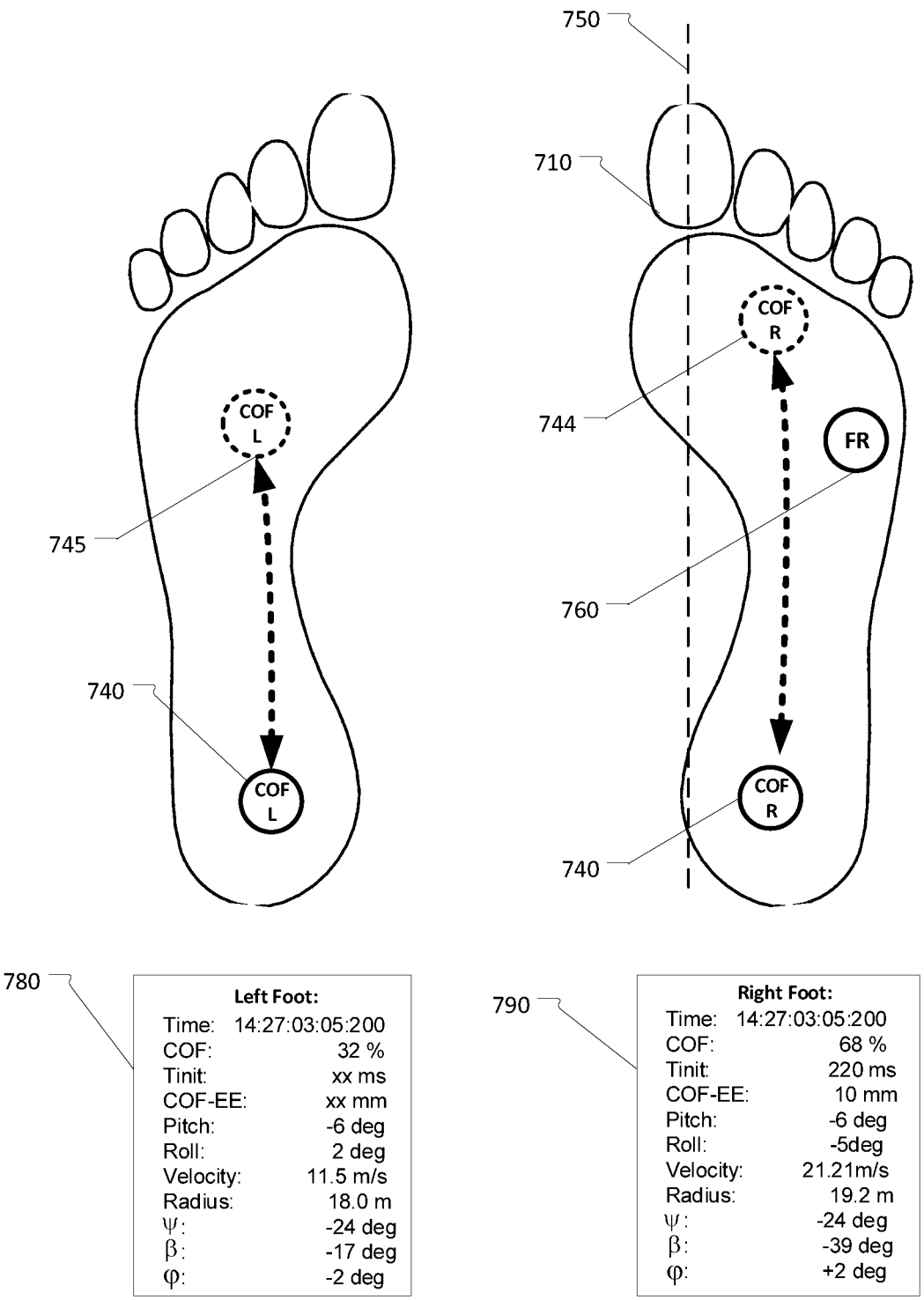
FIG. 15, presents graphical and numerical representation of motion and pressure points transmitted to the skiboot insole by the foot during an unsuccessful turn.

The graphical and numerical results, representing unsuccessful turn is presented in FIG. 15. Here we see the mistake user makes during the start of transition (flat ski⇒select new ski⇒COF of inner foot to head of $5^{th}$ MT), inner foot COF forward to the center of foot 744. In order to maintain balance the COF of the outer foot was placed between $2^{nd}$ $3^{rd}$ MT 745, and the resulting force moved to the outer edge of the outer foot. In this position the body kinematics does not allow for pelvic rotation and in effect, the COF return to the heels of the feet—balance is lost, turn can't be finished until balance is recovered during next flat ski.

Data are analyzed in relation to velocity, pitch and roll and effective radius of the turn and other numerical results 780 and 790 for left/right foot respectively, and may be used by both the amateurs to improve their skills, professionals during training, judges in analyzing performance of a free style or figure skating competition or even commentators during televised sports events. Furthermore, those results may be sorted and presented in various statistical formats selected by the viewer. An example of such statistical analysis may be use in training and evaluation of turn symmetry—one of most important parameter of measuring progress of a professional skier. Turn symmetry, is term used to describe a pressure applied during the left and right turn. The closer is the distribution of pressures between inner/outer ski during the left and right turns, the better will the skier perform. Such analysis is currently limited to visual observation by the coach of the racer during a run over a specific part of the slope where the transversal angle of the slope maintains relatively constant angle to the line of the slope. Such observation is subjective, prone to errors and of limited value—as it's impossible to evaluate the symmetry of pressure visually and specifically on the slope with changing topographical parameters.

Turn symmetry statistics can be performed as follows:

Log all left turns into LEFT_SET, and all right turns into RIGHT SET;

FOR each turn with $\Phi_L = \Phi_R$ OR $-\Phi_L = +\Phi_R$ OR $+\Phi_L = -\Phi_R$ (roll);

Extract pressure points and force data;

Sort pressure points and force data in the descending order of difference.

Similar method may be used for numerous other parameters of the run.

Figure 16:
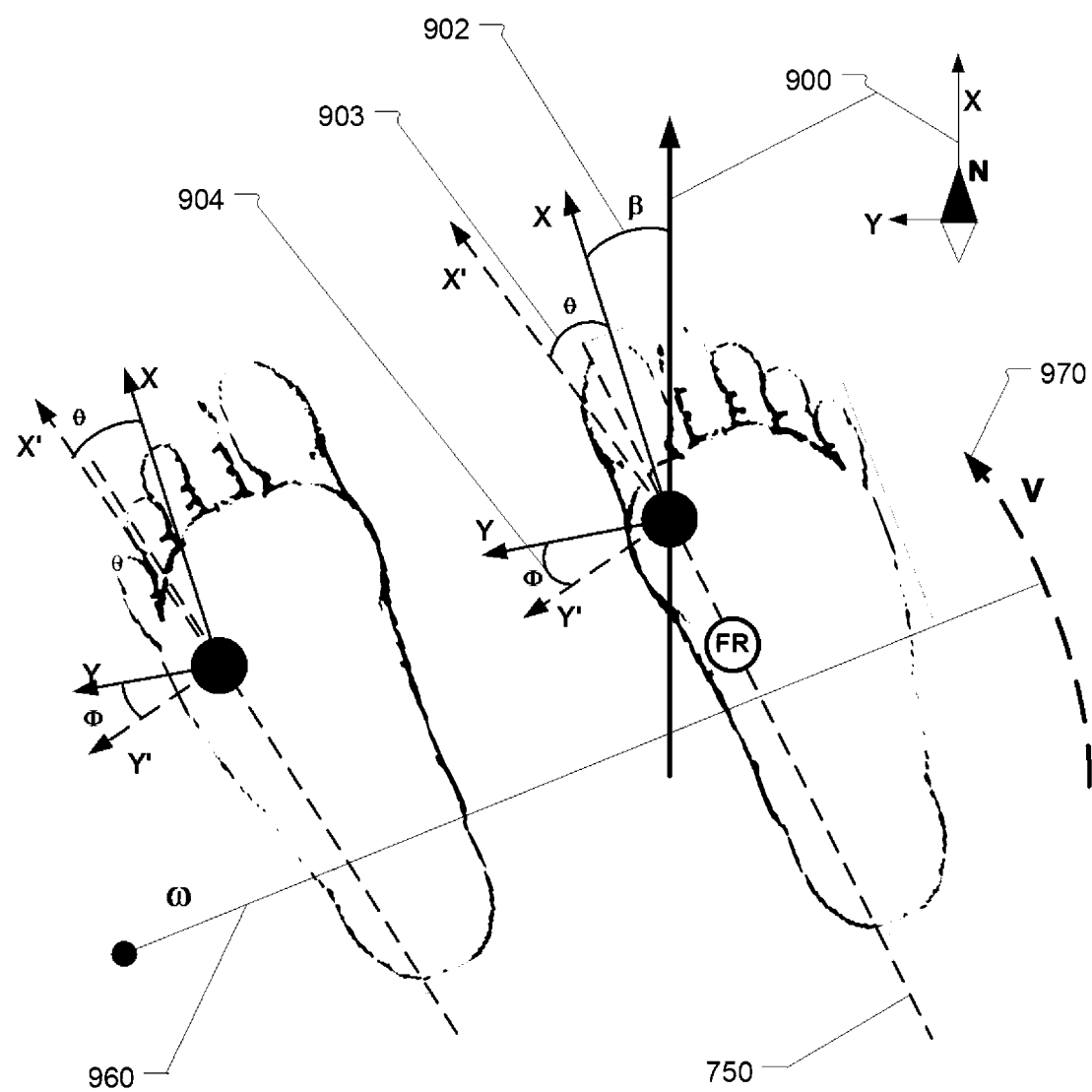
FIG. 16, presents another version of graphical representation of motion in relation to the pressure points on the skiboot insole.

Different view of the data presented in FIG. 16, where both feet are shown in relation to the global coordinate 900, the angle β, 902 to the local coordinate X, pitch Θ, 903, of the ski (angle between X and X)', the roll inside the turn Φ, 904, the effective turning radius ω, 960, and velocity V 970. The location of resulting force $F_R$ in relation to the ski edge 750 is also presented.

Another embodiment of skiing analyzer feedback system may employ direct control by an instructor of coach. Here, motion and force sensors data is relayed by the smart-phone 200, to the remote device 700, operated by instructor or coach, who maintains visual contact with the user. On the device 700, data is processed by application 300, enhanced with a user interface (UI), allowing to manually control the haptic feedback actuator embedded in the user skiboot insole. The input from the terminal 700, UI operated by instructor, is send back over wireless cellular interface 400 and 221, to the user smart-phone 200 and then using the PAN wireless interface 210 to the haptic feedback actuator 1033, located in insole 100. Such embodiment allows the couch to directly influence the user actions and tailor his training/progress according to predefined plan or changing slope conditions.

Description of Another Embodiment

This embodiment comprises a motion and force processing element and an haptic actuator element embedded in the user shoe insoles configured to analyze gait and balance by estimating vertical ground reaction force vector applied to the user feet and limbs in relation to feet motion and to provide haptic corrective feedback. In addition to motion, force and haptic elements, said embodiment comprises a wireless personal area network (PAN) transceiver—such as: Bluetooth, ANT, etc., used for transmission of force and motion data to the smart-phone based application and for reception of control signals intended for haptic feedback actuators. Based on the knowledge of gait bio-mechanics, and information received from the insoles, smart-phone based application provides haptic feedback to the user feet, suggesting proper timing and distribution of pressure points. Furthermore, the smart-phone application transmits gait data and the user GPS location coordinates to a remote location for post-processing using wireless cellular network.

In general, gait cycle comprises of two phases: 1) Stance Phase; and 2) Swing Phase, with the respective duration of those two phases of 60% and 40% of the user gait cycle. Furthermore, each phase of the cycle can be further divided into portions consisting of double or single limb support. It is those portion of each phase of the gait cycle, when the heel strikes the ground, limb swings or terminates the swing which are analyzed providing location of user Center of Mass (COM), and in conjunction with the location of Center of Pressure (COP), present picture of user balance and gait characteristics.

The position of COP can be obtained by placing several pressure sensors in shoe sole, then synchronizing the changes in COP with 3-dimensional motion vectors obtained from motion processing element. Knowledge COP location in the past combined with COP current location in relation to the movement of user in 3-dimensional space allows for prediction of movement of user feet during the next gait phase or even next gait cycle. Such knowledge may be used to provide a "advise"—in form of haptic feedback to the user foot, instructing of location of pressure and the timing said pressure must be applied in order to correct abnormal gait or to improve it's efficiency.

Figure 1B:
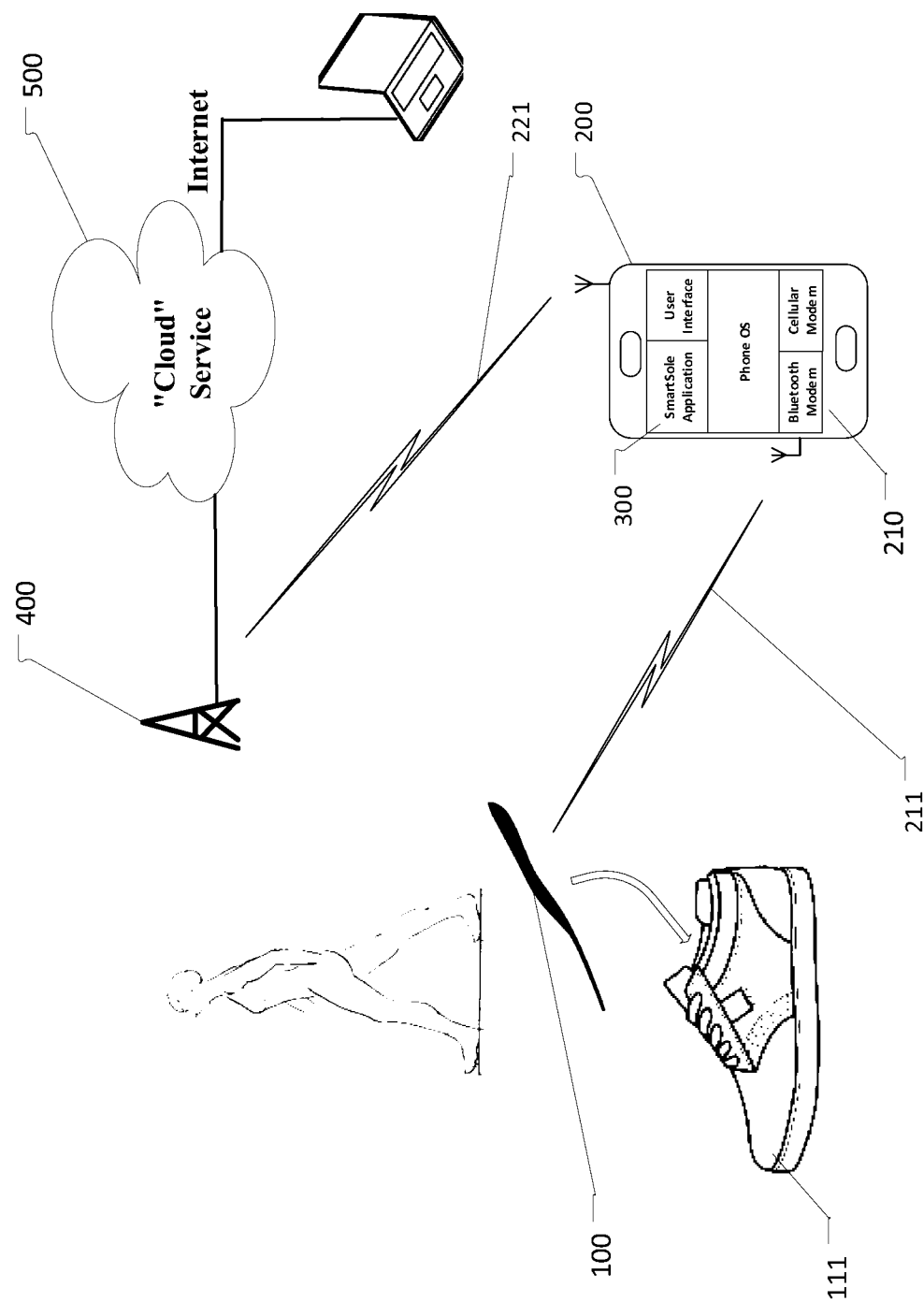
FIG. 1B, is an exemplary gait analysis haptic feedback system.

The exemplary system is presented in FIG. 1B. Here an insole 100, of a shoe 111, communicates with a monitoring application 300, hosted in a smart-phone 200. The monitoring application 300 pre-processes the motion and pressure data, retrieves a GPS time and coordinates from the smart-phone and sends said data using smart-phone cellular radio interface 221, to the cloud service 500, for further post-processing, while the pre-processed motion and pressure data are used to provide haptic feedback to the actuator located in the insole. Based on GPS coordinates extracted from data, a 3D map of the area may be superimposes on result graphical and numerical parameters displayed on remote computer on user smart-phone.

Gait analysis insole 100, presented on FIG. 2 and FIG. 3, comprises of a lower 101, and upper 102, insole surfaces and a motion processing and feedback sub-system 103, sandwiched in between insole surfaces. The processing sub-system, presented in FIG. 4, consist a motion processing element 1031, two or more force sensors 1032, and a haptic actuator 1033 and a Bluetooth RF transceiver 1036, a microprocessor 1034 and microprocessor program memory 1035. The motion processing element 1031, is configured for analysis of 3-dimensional motion comprises inertial MEMS sensors: a 3-axis gyroscope; a 3-axis accelerometer; a 3-axis magnetometer (compass); and an atmospheric pressure sensor, with sensors connected to the microprocessor 1034 using one of appropriate digital interfaces—such as I2C, or an appropriate analog interface. Similarly, the force pressure sensors are connected to the microprocessor analog-to-digital (ADC) converter inputs using appropriate analog interface or can be directly connected to the microprocessor digital interface, while the haptic feedback actuator may be connected to the microprocessor digital-to-analog (DAC) converter.

By observing three-dimensional vectors of gravity, orientation and azimuth one can determine current orientation of user feet motion. Motion of user foot, is calculated by, first converting gyroscope angular rate to a quaternion representation:

$$dq(t)/dt = \tfrac{1}{2}\omega(t)*q(t),$$

where ω(t) is the angular rate of motion and q(t) represents normalized quaternion. Then, converting the accelerometer results from local coordinate system, represented as $A_L$ to global coordinate system, represented as $A_G$, by using previously obtained quaternion as:

$$A_G(t) = q(t)*A_L(t)+q(t)'.$$

sand calculating acceleration quaternion as:

$$qf(t) = [0 A_{Gy}(t) - A_{Gz}(t) 0]*\text{gain}$$

which is added as a feedback term to quaternion from gyroscope, and follow with adding magnetometer data to the azimuth component.

Relation between ground force and user foot 710, is presented in FIG. 5. Here the insole 100, comprising motion processing element 1031, and force sensing elements 1032 and 1033 records the force $F_{TOE}$, 104 and $F_{HEEL}$, 105 applied by the user toes and heel in reaction to ground force while recording also the timing and location of the force in relation to 3-dimensional motion of the foot—those obtaining the location of the center-of-force (COF), and distribution of forces between feet.

Location of the pressure points is measured by force sensors 1032 placed inside the insoles. Said measurements end their relation to motion vectors are used to obtain location of the center-of-force (COF) and consequently the actual gait and are used to derive correction feedback 106, through the use of haptic actuator 1033.

Figure 18:
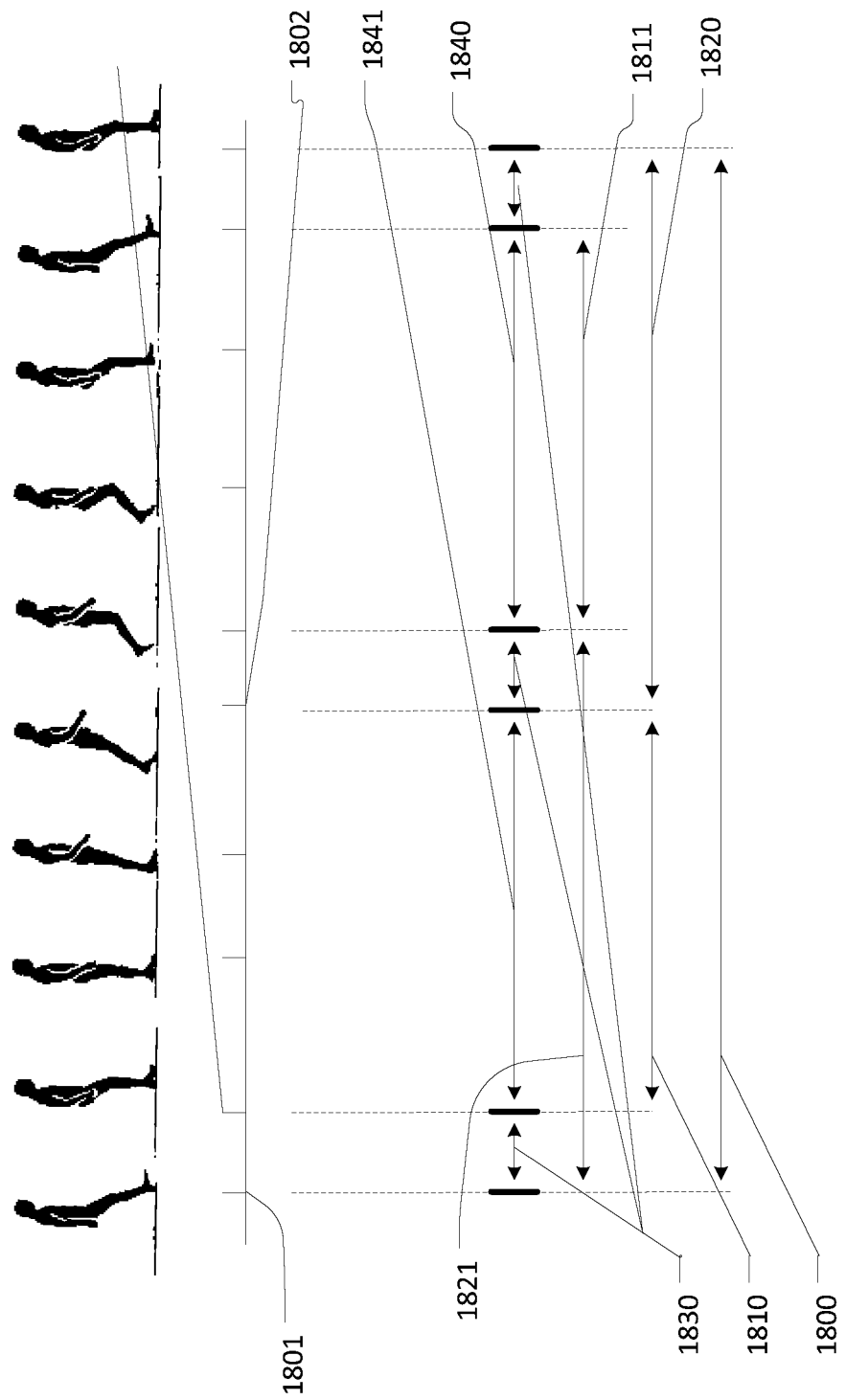
FIG. 18, presents typical cycle of the gait in relation to timing of cycle phases.

Process of walking or running is presented in FIG. 18. As the body moves forward one limb typically provides support while the other limb is advanced in preparation for its role as the support limb. The gait cycle 1800, is comprised of stance phase 1821, and swing phase 1811. The stance phase further is subdivided into 3 segments: 1) initial double stance 1830; 2) single limb stance; and 3) terminal double limb stance 1831. Each of double stance phases accounts for approximately 10% of the gait cycle, while the single stance typically represents about 60% of the total gait cycle, and the swing phase the remaining of the gait cycle. During double stance period, the two limbs do not typically share the load of the user and slight variations occur in the percentage of stance and swing in relation to velocity—with each aspect of stance decreasing as walking velocity increases. The transition from walking to running is marked by elimination of double support periods. In a normal gait cycle, the two steps comprising the cycle are roughly symmetric.

During walk or run, each stride contains eight relevant phases, a single cycle of such stride or gait cycle 1800, is presented in FIG. 18. Of those eight phases, five are allocated to a stance (i.e. initial contact, loading response, mid stance, terminal stance, pre-swing), 1820 and 1821 for the left and the right foot respectively, with the remaining 3 phases allocated to a swing 1810 and 1811 for the left and the right foot respectively. The first two gait phases occur during initial double support 1830, and include the initial contact with the ground and the ground loading response. In the normal gait, the initial contact is referred as a heel strike 1801 and 1802 for the right and the left foot respectively, also, many patients recovering from injuries, or with the gait pathology, achieve heel contact later in the cycle, or not at all. Two phases located between the double support phases are referred as a single support phase 1840 and 1841, for the left and right foot respectively. The joint motion during the double support phase allows transfer of weight from one to anther leg while attenuating shock, preserving gait velocity, and maintaining balance.

The swing phase corresponding to single support of the limb currently supporting body weight consisting of first half with a single support and termed mid-stance which is responsible progression of the center of mass over the support foot and includes heel rise of the support foot and terminates with ground contact of the other foot. The final stance element—pre-swing, is related functionally to the swing phase that follows and begins with terminal double support and ends with toe-off of the limb.

Many user specific parameters, must be considered in gait analysis. Some of those parameters, for example: the user weight of sex, may be entered through the application User Interface (UI), others, such as: the user's gait pathological conditions, may be obtained during self-calibration procedures; while yet another—for example: configuration of the terrain, speed of movement, atmospheric conditions, etc. may be collected in real time from the smart-phone GPS receiver and sensors.

User specific parameters comprise several information, such as: 1) physical and physiological information; 2) physiological information; 3) pathological information; and 4) static gait information.

The first information comprises description of user physical characteristics—sex (male/female); weight; height and a body-type. The second information comprising description of user physiological characteristics—distance from hip to knee, and knee to ankle. The third information comprising description user pathological characteristics—trauma/injuries, muscular abnormalities. The forth information comprising description of normal, abnormal or pathological gait is obtained by the system during calibration procedures.

The first and the second information can entered through the smart-phone user interface (UI). The third information can be entered through the smart-phone UI, or downloaded from the remote medical facility. The forth information is obtained by the analyzer during initial calibration procedures.

During dynamic (walk, run) gait analysis the third information obtained during static calibration which provides empirical information of user posture, foot orientation, natural distribution of pressure inside the shoe is used as a coefficient in a filter (may be of an interpolating, or an extrapolating of a Kalman form), which in turn may be used as an input to the haptic stimulus function intended to modify the abnormality of gait—for example: abnormal gait is due to an injury and needs to be corrected.

Figure 19A:
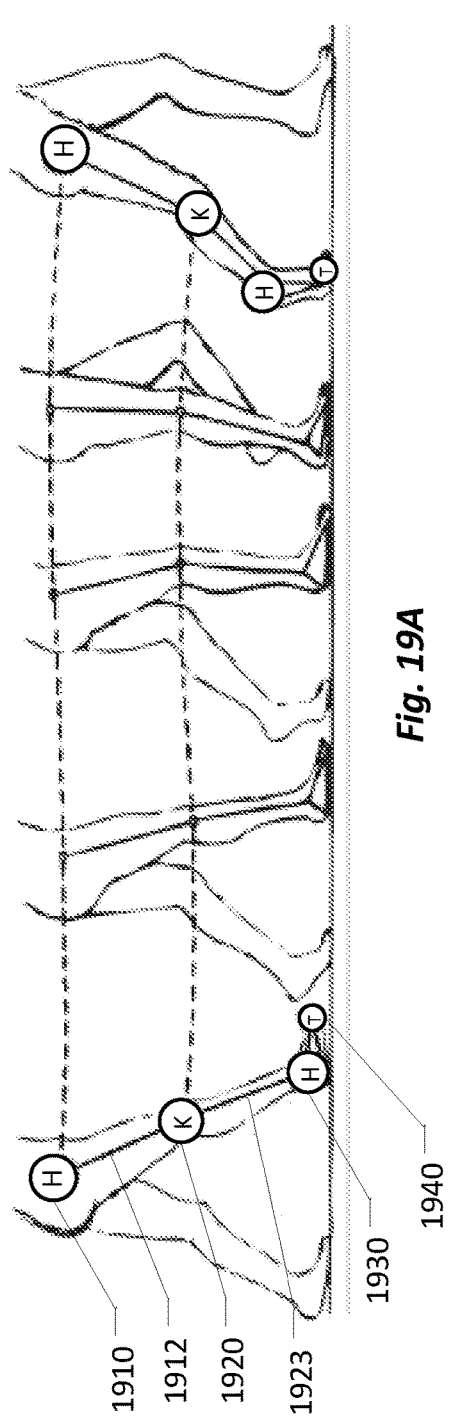
FIG. 19A, presents model used to analyze moments and forces applied to joints'

The results of dynamic gait analysis provides values and distribution of ground reaction force experienced by the user foot in relation to feet motion in time, does providing full picture of the user gait. Those results can provide an estimate of rotation moments in each individual joint and used by the analyzer to calculate—and communicate in form of haptic feedback, the proper location of pressure the use must applied during the next gait cycle. An exemplary presentation of the location and the distribution of COF were discussed in detail in previous paragraphs and are presented FIGS. 6A, 6B, 6C; 7A, 7B, 14 and 15, and the model of joints (hip 1910; knee 1920, heel 1930, and toe 1940) used to analyze moments and forces applied to joints is presented in FIG. 19A. Assuming the knowledge of the user physical characteristics (sex, weight, height, body type contained in the first information), and his physiological characteristics (distance from hip to knee 1912, and knee to ankle 1923), one knowing the location, value and distribution of ground reaction force on the user feet obtained from the force sensors; plus the phase of the gait and timing obtained from the motion processing element; plus the location and terrain characteristics obtained from the smart-phone GPS receiver—may estimate forces and rotation vectors present in each joint.

Figure 19B:
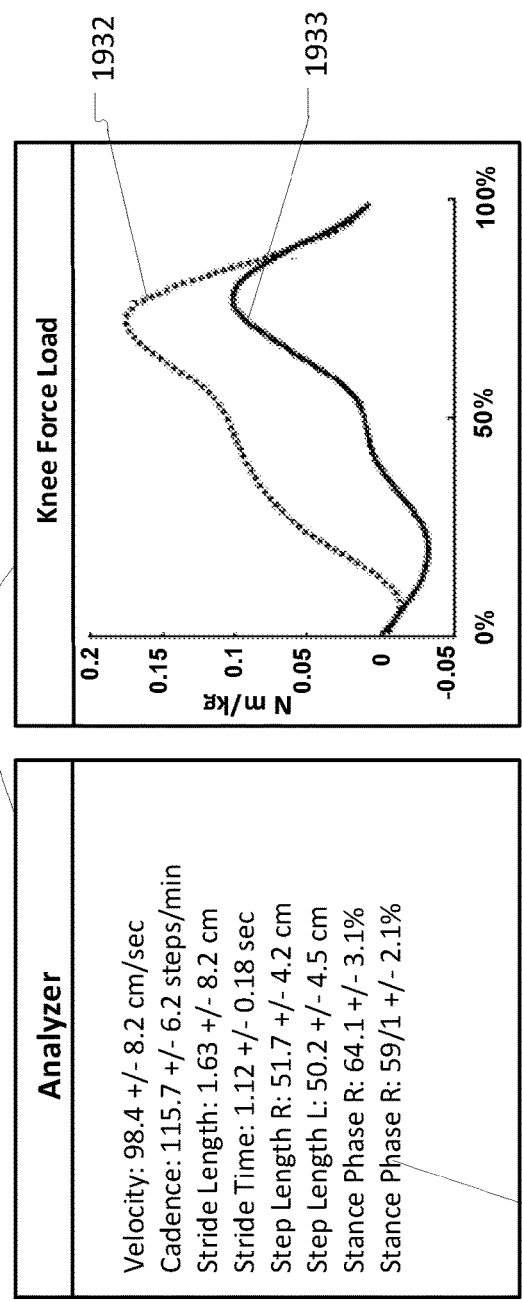
FIG. 19B, presents an example of an analysis of ankle during the stride with numerical data and in graphical form during sampling time of the averaged gait cycle.

The results obtained in said analysis of gait may be presented in various formats, for example: numerical; graphical or statistical. An exemplary representation of said results is presented in FIG. 19A and FIG. 19B. In this example, an analysis of ankle 1930, during the stride with statistical numerical data 1931 is presented in graphical form, providing picture of load (force) to the right ankle 1932, and the right ankle 1033 at each sampling time of the averaged gait cycle.

When the gait analyzer residing in the user smart-phone is enabled, the phone Bluetooth establishes wireless communication with the left and the right shoe insoles. At this time analyzer associates left and right insoles Bluetooth devices ID (such as the device UUID identification), with the left/right foot and prompts the user may to enter (or download): first; second; and third user information. Then, prompts the user to perform calibration of his natural stance—forth information.

This calibration is performed in two separate phases: first phase—the insoles orientation within the specific user shoes is calibrated to accommodate for a different type of shoes (walking, running shoes, different inclination, tilt, etc.); second phase—the user is instructed to step inside the shoes and retain several predefined positions designed to obtain the distribution weight between user feet, distribution of pressure pints within the shoes, does obtaining the user natural posture as well as verification of user's actual weight versus the weight recorded in the first information. The results of this calibration are used to define the difference between the user actual gait and the desired gait. Such difference is entered as a coefficient into the Least Mean Squares (LMS), or a Gradient algorithm or another appropriate filter—such as Kalman filter, designed to minimize the difference between the current gait and the optimal gate by stimulating feedback function applied to the haptic actuators locate in the insoles. Such feedback function may be delivered in form of haptic pulses of various amplitudes and frequencies using vibrating actuator located in a specific place inside the shoe insole—for example under the user big toe, or by a multiplicity of such actuators located in a designated areas of the insoles.

The motion and ground reaction force is processed against the user body model obtained from the second information (user physiological characteristics), using inertia navigation algorithms and geometrical triangulation, translating sensors kinematics to user body segments kinematics by measuring position (and timing) of center of force (COF), and a biomechanical model of foot/surface interface during gait cycle. The results may be uploaded to the remote computer server for further processing or display using the smartphone cellular radio interface.

The numerical results may be stored in CSV or XLS file formats and made available for visualization of the moments and forces superimposed over graphical representation of human body and/or over terrain or 3-D maps generated from collected GPS, atmospheric pressure or other sensors data. Additionally, said stored data can be viewed in wide range of statistical analysis tools in form of graphs, distribution functions, etc.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications and variations that fall within the spirit and scope of the appended claims. Furthermore, to the extent that the terms "includes", "has" or "having" are used in either the detailed description or the claims, such terms are intended to be inclusive in a manner similar to the term "comprising" as "comprising" is interpreted when employed as a transitional word in a claim.

It is understood that the specific order or hierarchy of steps in the processes disclosed is an example of exemplary approaches. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented Those of skill in the art would understand that information and signals may be represented using any of a variety of different technologies and techniques. For example, data, instructions, commands, information, signals, symbols, etc. may be referenced throughout the above description by other means.

Those of skill would further appreciate that the various illustrative logical blocks, modules, and algorithmic steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

What is claimed:

1. A gait and balance system designed to measure motion indicative of a selected user's gait and balance, comprising:
    (a) an insole for use with a selected user's foot and shaped to be inserted into foot apparel worn by the selected user, wherein the insole comprises:
        (1) a lower insole portion;
        (2) an upper insole portion; and
        (3) a motion processing and feedback subsystem positioned proximate to and between the lower insole portion and the upper insole portion, and wherein the motion processing and feedback subsystem comprises:
            (A) a motion processing device, comprising:
                1) A 3-axis gyroscope generating 3-axis x, y and z orientation vectors;
                2) A 3-axis accelerometer generating 3-axis x, y and z gravity vectors;
                3) A 3-axis magnetometer generating 3-axis x, y and z magnetic field vectors; and
                4) an atmospheric pressure sensor generating atmospheric pressure sensor data; wherein the 3-axis orientation vectors, the 3-axis x, y and z gravity vectors, the 3-axis magnetic field vectors and the atmospheric pressure sensor data collectively comprise motion data generated by the motion processing device;
            (B) a plurality of force pressure sensors placed under the selected user's feet generating force pressure data;
            (C) a haptic feedback actuator;
            (D) a wireless communication input/output device;
            (E) a microprocessor; wherein the motion processing device, the plurality of force pressure sensors and the haptic feedback actuator communicate with the microprocessor using a communications interface; and
            (F) a memory storage device capable of storing software programs and related data for use by the microprocessor;
    (b) a smart phone that executes a monitoring software application that monitors the selected user's activity, wherein the monitoring software application processes the motion data and the force pressure data to obtain a distribution of ground reaction forces (GRF) at the selected user's feet thereby determining a location of a center of pressure (COP), wherein the COP comprises a weighted average of the force pressure data, and wherein the smart phone determines GPS timing and coordinate information and synchronizes the GPS timing and coordinate information with the motion and force pressure data thereby generating GPS synchronized motion and force pressure data, and wherein the smart phone and the monitoring software application communicates with the motion processing and feedback subsystem, via the wireless communication input/output device; and (c) a cloud-based server; wherein the cloud-based server processes the GPS synchronized motion and force pressure data and generates foot motion and force distribution information related to the selected user;

and wherein the gait and balance system determines a gait of the selected user based upon a stance phase and a swing phase of a gait cycle for the selected user, and wherein the stance phase comprises a plurality of segments, and wherein each segment of the stance phase and the swing phase is determined by continuously monitoring the location of the COP and the magnitude of the GRF present at the COP location and the distribution of the GRF between the selected user's left and right foot in relation to the 3-axis orientation, gravity and magnetic field vectors.

2. The gait and balance system of claim 1, wherein wherein the motion processing device determines:

a calibrated reference of the selected user's body weight using the selected user's physical characteristics and measurements of force present at the selected user's feet, using a weighted average of the measurements of force that determine the location of the center of pressure (COP) and the distribution of force between the selected user's left and right foot, a calibrated reference of the selected user's natural pronation parameters by obtaining global coordinates and local coordinates of the selected user's feet, a location of center of mass (COM) using the selected user's physical and physiological information related to the selected user, and a gravity vector at the COP location;

and wherein the global coordinates of the selected user's feet are obtained by measuring the global coordinates at the selected user's current geographical location.

3. The system of claim 2, wherein natural pronation parameters of the selected user are obtained by recording a magnitude of a GRF applied to the selected user's feet while the selected user remains in a natural standing position in relation to the 3-axis x, y and z orientation vectors and the 3-axis x, y, and z gravity vectors.

4. The system of claim 3, wherein the GRF present at the selected user's foot COP is determined by calculating a g-force based upon the x, y and z gravity vectors and multiplying the calculated g-force by a sum of the selected user's calibrated weight.

5. The system of claim 4, wherein the calibrated weight of the selected user is obtained by comparing ½ of a declared weight of the selected user with the force pressure data measured by the plurality of force pressure sensors, and if the difference between the declared weight and the force pressure data is larger than ½ of the declared weight the difference is stored as a negative offset of a respective force pressure sensor, and if the difference is smaller than ½ of the declared weight said difference is stored as a positive offset of the respective force pressure sensor.

6. The system of claim 1, wherein motion of the selected user's feet in three-dimensional space is estimated by collecting instantaneous changes in the gravity, orientation and magnetic field vectors received from the accelerometer, the gyroscope and the magnetometer, respectively, and by calculating angular changes of the gravity, orientation and magnetic field vectors, and by integrating the angular changes of the gravity, orientation and magnetic field vectors over a selected period of time.

7. The system of claim 1, wherein a location of a center of mass (COM) of the selected user is obtained by performing a weighted average of each body segment obtained from the selected user's kinematics during each phase of the selected user's gait cycle.

8. The system of claim 1, wherein a physiological characteristic of the selected user comprises information of a distance between the selected user's hip and knee and a distance between the selected user's knee and ankle.

9. The system of claim 1, wherein a natural stance characteristic of the selected user comprises information about the selected user's normal gait, abnormal gait-pronation, over-pronation, supination, and over-supination.

\* \* \* \* \*